United States Patent
Borras et al.

(10) Patent No.: US 10,087,244 B2
(45) Date of Patent: *Oct. 2, 2018

(54) HUMANIZATION OF RABBIT ANTIBODIES USING A UNIVERSAL ANTIBODY FRAMEWORK

(71) Applicant: ESBATech, an Alcon Biomedical Research Unit LLC, Schlieren (CH)

(72) Inventors: Leonardo Jose Borras, Schlieren (CH); David Urech, Hombrechtikon (CH)

(73) Assignee: ESBATech, an Alcon Biomedical Research Unit LLC, Shlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/965,488

(22) Filed: Dec. 10, 2015

(65) Prior Publication Data

US 2016/0096903 A1 Apr. 7, 2016

Related U.S. Application Data

(62) Division of application No. 14/179,141, filed on Feb. 12, 2014, now abandoned, which is a division of application No. 13/616,214, filed on Sep. 14, 2012, now Pat. No. 8,937,162, which is a division of application No. 13/000,309, filed as application No. PCT/CH2009/000222 on Jun. 25, 2009, now Pat. No. 8,293,235.

(60) Provisional application No. 61/075,697, filed on Jun. 25, 2008, provisional application No. 61/155,041, filed on Feb. 24, 2009, provisional application No. 61/155,105, filed on Feb. 24, 2009.

(51) Int. Cl.
| | |
|---|---|
| *C07K 14/465* | (2006.01) |
| *C07K 16/18* | (2006.01) |
| *C07K 16/22* | (2006.01) |
| *C07K 16/24* | (2006.01) |
| *A61K 39/395* | (2006.01) |
| *C07K 16/30* | (2006.01) |
| *C07K 16/46* | (2006.01) |
| *A61K 47/68* | (2017.01) |

(52) U.S. Cl.
CPC .......... *C07K 16/18* (2013.01); *A61K 39/3955* (2013.01); *A61K 39/39558* (2013.01); *A61K 47/6877* (2017.08); *C07K 16/22* (2013.01); *C07K 16/241* (2013.01); *C07K 16/30* (2013.01); *C07K 16/465* (2013.01); *C07K 2317/24* (2013.01); *C07K 2317/31* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2317/76* (2013.01); *C07K 2317/92* (2013.01); *C07K 2317/94* (2013.01); *C07K 2319/30* (2013.01)

(58) Field of Classification Search
CPC .............. C07K 14/465; C07K 2317/24; C07K 2317/567; C07K 2317/565; A61K 47/6877
USPC .................................... 424/133.1; 530/387.3
See application file for complete search history.

(56) References Cited

U.S. PATENT DOCUMENTS

| | | | |
|---|---|---|---|
| 4,704,362 A | 11/1987 | Itakura et al. | |
| 4,881,175 A | 11/1989 | Ladner | |
| 4,946,778 A | 8/1990 | Ladner et al. | |
| 5,013,653 A | 5/1991 | Huston et al. | |
| 5,091,513 A | 2/1992 | Huston et al. | |
| 5,132,405 A | 7/1992 | Huston et al. | |
| 5,225,539 A | 7/1993 | Winter | |
| 5,258,498 A | 11/1993 | Huston et al. | |
| 5,260,203 A | 11/1993 | Ladner et al. | |
| 5,304,489 A | 4/1994 | Rosen | |
| 5,455,030 A | 10/1995 | Ladner et al. | |
| 5,476,786 A | 12/1995 | Huston | |
| 5,482,858 A | 1/1996 | Huston et al. | |
| 5,693,761 A | 12/1997 | Queen et al. | |
| 5,741,957 A | 4/1998 | Deboer et al. | |
| 5,837,821 A | 11/1998 | Wu | |
| 5,849,992 A | 12/1998 | Meade et al. | |
| 6,815,540 B1 | 11/2004 | Pluckthun et al. | |
| 7,429,487 B2 | 9/2008 | Pytela et al. | |
| 8,937,162 B2 * | 1/2015 | Borras ................... | C07K 16/22 424/133.1 |
| 2005/0033031 A1 | 2/2005 | Couto et al. | |
| 2005/0048578 A1 | 3/2005 | Zhang | |
| 2006/0216293 A1 | 9/2006 | Couto et al. | |
| 2011/0159007 A1 | 6/2011 | Borras et al. | |

FOREIGN PATENT DOCUMENTS

| | | |
|---|---|---|
| EP | 1918302 A2 | 7/2008 |
| RU | 2297245 C2 | 4/2007 |
| WO | 1986001533 A1 | 3/1986 |

(Continued)

OTHER PUBLICATIONS

Borras et al. The Journal of Biological Chemistry vol. 285, No. 12, pp. 9054-9066, Mar. 19, 2010.*

(Continued)

*Primary Examiner* — Lynn A Bristol
(74) *Attorney, Agent, or Firm* — Jason J. Derry

(57) ABSTRACT

The present invention relates to an universal antibody acceptor framework and to methods for grafting non-human antibodies, e.g., rabbit antibodies, using a universal antibody acceptor framework. Antibodies generated by the methods of the invention are useful in a variety of diagnostic and therapeutic applications.

2 Claims, 6 Drawing Sheets
Specification includes a Sequence Listing.

(56) References Cited

FOREIGN PATENT DOCUMENTS

| | | |
|---|---|---|
| WO | 199007861 A1 | 7/1990 |
| WO | 199409817 | 5/1994 |
| WO | 0130393 A2 | 5/2001 |
| WO | 200148017 A1 | 7/2001 |
| WO | 200202781 A1 | 1/2002 |
| WO | 2002012502 | 2/2002 |
| WO | 03074679 A2 | 9/2003 |
| WO | 2003097697 A2 | 11/2003 |
| WO | 2004016740 A2 | 2/2004 |
| WO | 2004087216 A2 | 10/2004 |
| WO | 2004087216 A3 | 10/2004 |
| WO | 2005016950 A1 | 2/2005 |
| WO | 2005035575 A2 | 4/2005 |
| WO | 2006131013 A2 | 12/2006 |
| WO | 2007-001851 A2 | 1/2007 |
| WO | 2007042775 A2 | 4/2007 |
| WO | 2007042809 A2 | 4/2007 |
| WO | 2007047112 A2 | 4/2007 |
| WO | 2007124610 A1 | 11/2007 |
| WO | 2007140371 A2 | 12/2007 |
| WO | 2008004834 A1 | 1/2008 |
| WO | 2008006235 A2 | 1/2008 |
| WO | 2008110348 A1 | 9/2008 |
| WO | 2008118356 | 10/2008 |
| WO | 2008144757 A1 | 11/2008 |
| WO | 2009000098 A2 | 12/2008 |
| WO | 2009000099 A2 | 12/2008 |
| WO | 2009155725 A1 | 12/2009 |
| WO | 2009155726 A2 | 12/2009 |

OTHER PUBLICATIONS

Pan et al., "Blocking neuropilin-1 function has an additive effect with anti-VEGF to inhibit tumor growth", Cancer Cell, 2007, vol. 11, pp. 53-67.

Roitt et al., "Immunology", 2000, Mir. Moscow, pp. 97-106.

Rader et al., "The rabbit antibody repertoire as a novel source for the generation of therapeutic human antibodies", The Journal of Biological Chemistry, 1999, vol. 275, No. 18, pp. 13668-13676.

Roovers et al., "Efficient inhibition of EGFR signalling and of tumour growth by antagonistic anti-EGFR nanobodies", Cancer Immunol. Immunother; 2007, vol. 56, pp. 303-317.

Roguska et al., "A comparison of two murine monoclonal antibodies humanized by CDR-grafting and variable domain resurfacting", Protein Engineering, 1996, vol. 9, No. 10, pp. 895-904.

Colman et al., "Effects of amino acid sequence changes on antibody-antigen interactions", Research in Immunology, 1994, vol. 145, pp. 33-36.

Depascalis et al., "Grafting of 'abbreviated' complementarity-determining regions containing specificity-determining residues essential for ligand contact to engineer a less immunogenic humanized monoclonal antibody", The Journal of Immunology, 2002, vol. 169, pp. 3076-3084.

Dufner et al., "Harnessing phage and ribosome display for antibody optimization", Trends in Biotechnology, 2006, vol. 24, No. 11, pp. 523-529.

Vajdos et al., "Comprehensive functional maps of the antigen-binding site of an anti-ErbB2 antibody obtained with shotgun scanning mutagenesis", Journal of Mol. Biol.,1999, vol. 320, pp. 415-428.

Wu et al., "Humanization of a murine monoclonal antibody by simultaneous optimization of framework and CDR residues", Journal of Mol. Biol., 1999, vol. 294, pp. 151-162.

International Search Report corresponding to PCT Application Serial No. PCT/CH2009/000222.

Written Opinion corresponding to PCT Application Serial No. PCT/CH2009/000222.

Alfthan et al.; "Properties of a single-chain antibody containing different linker peptides"; Protein Engineering; vol. 8; No. 7; pp. 725-731 (1995).

Allen; "Ligand-targeted therapeutics in anticancer therapy"; Reviews; Nature; vol. 2; pp. 750-763 (Oct. 2002).

Auf Der Maur et al; "Antigen independent selection of stable intracellular single-chain antibodies"; FEBS Letters: vol. 508; pp. 407-412 (2001).

Bird et al; "Single-chain antigen-binding proteins"; Science; vol. 242; pp. 423-426; (Oct. 21, 1988).

Boulianne et al.; "Production of functional chimaeric mouse/human antibody"; Letters to nature; Nature; vol. 312; pp. 643-646 (Dec. 13, 1984).

Brennan; "Preparation of bispecific antibodies by chemical recombination of monoclonal immunoglobulin G1 fragments"; Science; vol. 229; pp. 81-83 (Jul. 5, 1985).

Carter et al; "Improved oligonucleotide site-directed mutagenesis using M13 vectors"; Nucleic Acids Research; vol. 13; No. 12; pp. 4431-4443; (1985).

Choi et al; "Recombinant chimeric OKT3 scFv IgM antibodies mediate immune suppression while reducing T cell activation in vitro"; Eur. J. immunol.; vol. 31; pp. 94-106 (2001).

Clark; Antibody humanization: a case of the 'Emperor's new clothes'?; review; Immunology today; vol. 21; No. 8; pp. 397-402.

Zubler et al.; "Mutant EL-4 thymoma cells polyclonally activate murine and human B ells via direct cell interaction"; The Journal of Immunology; vol. 134; No. 6; pp. 3662-3668 (Jun. 1985).

Roovers et al.; "In vitro characterisation of a monovalent and bivalent form of a fully human anti Ep-CAM phage antibody"; Cancer Immunol Immunother; vol. 50; No. 1; pp. 51-59 (2001).

Roovers et al.; "Efficient inhibition of EGFR signalling and of tumour growth by antagonistic anti-EGFR nanobodies"; Cancer Immunol. Immunother; vol. 56; pp. 303-317 (2007).

Roguska et al.; "A comparison of two murine monoclonal antibodies humanized by CDR-grafting and variable domain resurfacing"; Protein Engineering; vol. 9; No. 10; pp. 895-904 (1006).

Colman; Effects of amino acid sequence changes on antibody-antigen interactions; Research in Immunology; vol. 145; pp. 33-36 (1994).

Depascalis et al.; "Grafting of "abbreviated" complementarity-determining regions containing specificity-determining residues essential for ligand contact to engineer a less immunogenic humanized monoclonal antibody"; The Journal of Immunology; vol. 169; pp. 3076-3084 (2002).

Dufner et al.; "Harnessing phage and ribosome display for antibody optimization"; Trends in Biotechnology; vol. 24; No. 11; pp. 523-529 (2006).

Vajdos et al.; "Comprehensive functional maps of the antigen-binding site of an anti-ErbB2 antibody obtained with shotgun scanning mutagenesis"; J. Mol. Biol.; vol. 320; pp. 415-428 (1999).

Wu et al.; "Humanization of a murine monoclonal antibody by simultaneous optimization of framework and CDR residues"; J. Mol. Biol.; vol. 294; pp. 151-162 (1999).

Co et al; "Chimeric and humanized antibodies with specificity for the CD33 antigen"; The Journal of Immunology; vol. 148; pp. 1149-1154 (Feb. 15, 1992).

Dillman et al.; "Human anti-mouse antibody response in cancer patients following single low-dose injections of radiolabeled murine monoclonal antibodies"; vol. 9; No. 1; pp. 17-29 (1994).

Dumoulin et al; "Single-domain antibody fragments with high conformational stability"; Protein Science; vol. 11; pp. 500-515 (2002).

Ewert et al.; "Structure-based improvement of the biophysical properties of immunoglobulin VH domains with a generalizable approach"; Biochemistry, American Chemical Society; vol. 42; No. 6; pp. 1517-1528 (Feb. 18, 2003).

Ewert et al.; "Stability improvement of antibodies for extracellular and intracellular applications: CDR grafting to stable frameworks and structure-based framework engineering"; Methods: A Companion to Methods in Enzymology; vol. 34; No. 2; pp. 184-199 (Oct. 1, 2004).

Furrer et al.; "Pharmacokinetics and posterior segment biodistribution of ESBA105, an anti-TNF-alpha single-chain antibody, upon topical administration to the rabbit"; Investigative Ophthalmology & Visual Science; vol. 50; No. 2; pp. 771-778 (Feb. 1, 2009).

(56) References Cited

OTHER PUBLICATIONS

Gawaz et al.; "LIgand bridging mediates integrin allphallbbeta3 (Platelet GPIIB-IIIA) dependent homotypic and heterotypic cell-cell interactions"; J. Clin. Invest.; vol. 88; pp. 1128-1134 (Oct. 1991).
Glennie et al.; "Preparation and performance of bispecific F(ab'y)2 antibody containing thioether-linked Fab'y fragments"; The Journal of Immunology; vol. 139; No. 7; pp. 2367-2375 (Oct. 1, 1987).
Hamers-Casterman et al; "Naturally occurring antibodies devoid of light chains"; Letters to Nature; vol. 363; pp. 446-448 (Jun. 3, 1993).
Ho et al; "Site-directed mutagenesis by overlap extension using the polymerase chain reaction"; Gene; vol. 77; pp. 51-59 (1989).
Holliger et al; "Diabodies: small bivalent and bispecific antibody fragments"; Proc. Natl. Acad. Sci.; vol. 90; pp. 6444-6448 (Jul. 1993).
Carro, et al.; "Serum insulin-like growth factor I regulates brain amyloid-β levels"; Nature Publishing Group; published online Nov. 4, 2002 (http://www.nature.com/naturemedicine); vol. 8; No. 12; pp. 1390-1397.
Kashmiri, et al.; "SDR grafting—a new approach to antibody humanization"; Methods; Laboratory of Tumor Immunology and Biology, Center for Cancer Research, National Cancer Institute, National Institutes of Health, Bethesda, MD; 2005; No. 36; pp. 25-34.
Honegger and Pluckthun; "Yet another numbering scheme for immunoglobulin variable domains: an automatic modeling and analysis tool"; J. Mol. Biol.; vol. 309; pp. 657-670 (2001).
Hu et al; "Minibody: a novel engineered anti-carcinoembryonic antigen antibody fragment (single-chain Fv-CH3) which exhibits reapid, high-level targeting of xenografts"; Cancer Research; vol. 56; pp. 3055-3061 (Jul. 1, 1996).
Houston et al; "Protein engineering of antibody binding sites: recovery of specific activity in an anti-digoxin single-chain Fv analogue produced in *Escherichia coli*"; Proc. natl. Acad. Sci.; vol. 85; pp. 5879-5883 (Aug. 1988).
Jung et al.; "Improving in vivo folding and stability of a single-chain FV antibody fragment by loop grafting"; Protein Engineering; vol. 10; No. 8; pp. 959-966 (Jan. 1, 1997).
Karpovsky et al.; "Productin of target-specific effector cells using hetero-cross-linked aggregates containing anti-target cell and anti-Fcy receptor antibodies"; Journal of Experimental Medicine; vol. 160; pp. 1686-17041 (Dec. 1984).
Kipriyanov et al; "Bispecific tandem diabody for tumor therapy with improved antigen binding and pharmacokinetics"; J. Mol. Biol.; vol. 293; pp. 41-56 (1999).
Knappik et al; "Fully synthetic human combinatorial antibody libraries (HuCAL) based on modular consensus frameworks and CDRs randomized with trinucleotides"; J. Mol. Biol.; vol. 296; pp. 57-86 (2000).
Kugler et al.; "Stabilizatin and humanization of a single-chain Fv antibody fragment specific for human lymphocyte antigen CD19 by designed point mutations and CDR-grafting onto a human framework"; Protein Engineering, Design & Selection; vol. 22; No. 3; pp. 135-147 (Feb. 1, 2009).
Kunkel; Rapid and efficient site-specfiic mutagenesis without phenotypic selection; Proc. Natl. Acad. Sci.; vol. 82; pp. 488-492 (Jan. 1985).
Leong and Hibma; "A flow cytometry-based assay for the measurement of protein regulatin of E-cadherin-mediated adhesion"; Journal of Immunological Methods; vol. 302; pp. 116-124 (2005).
Liu et al.; "Heteroantibody duplexes target cells for lysis by cytotoxic T lymphocytes"; Proc. Natl. Acad. Sci.; vol. 82; pp. 8648-8652 (Dec. 1985).
Lobuglio et al; "Mouse/human chimeric monoclonal antibody in man: Kinetics and immune response"; Proc. Natl.; Acad. Sci.; vol. 86; pp. 4220-4224 (Jun. 1989).

Milenic et al; "Construction, binding properties, metabolism, and tumor targeting of a single-chain Fv derived form the pancarcinoma monoclonal antibody CC49"; Cancer Research; vol. 51; pp. 6363-6371 (Dec. 1, 1991).
Needleman and Wunsch; "A general method applicable to the search for similarities in the amino acid sequence of two proteins"; J. Mol. Biol.; vol. 48; pp. 443-453 (1970).
Ottiger et al.; "Efficient intraocular penetration of topical anti-TNF-alpha single-chain antibody (ESBA105) to anterior and posterior segment without penetration enhancer"; Investigative Ophthalmology and Visual Science; vol. 50; No. 2; pp. 779-786 (Feb. 1, 2009).
Panorchan et al.; Single-molecule analysis of cadherin-mediated cell-cell adhesion; Journal of Cell Science; vol. 119; pp: 66-74; (2006).
Pantolano et al; "Conformational stability, folding, and ligand-binding affinity of single-chain Fv immunoglobulin fragments expressed in *Eschericha coli*"; Biochemistry; vol. 30; pp. 10117-10125 (1991).
Pastan and Kreitman; Overview; Immunotoxins in cancer therapy; Current Opinion in Investigational Drugs; vol. 3; No. 7; pp. 1089-1091 (2002).
Paulus; "Preparation and biomedical applications of bispecific antibodies"; Behring INst. Mitt.; No. 78; pp. 118-132 (1985).
Payne; "Progress in immunoconjugate cancer therapeutics"; Cancer Cell; vol. 3; pp. 207-212 (Mar. 2003).
Popkov et al.; "Rabbit immune repertoires as sources for therapeutic monoclonal antibodies: the impact of kappa allotype-correlated variation in cysteine content on antibody libraries selected by phage display"; Journal of Molecular Biology; vol. 325; No. 2; pp. 325-335 (Jan. 10, 2003).
Queen et al; "Cell-type specific regulation of a k immunoglobulin gene by promoter and enhancer elements"; Immunological Reviews; pp. 49-68 (1986).
Riechmann et al; "Reshaping human antibodies for therapy"; Nature; vol. 332; pp. 323-327 (Mar. 24, 1988).
Rocha et al.; "Rabbit monoclonal antibodies show higher sensitivity than mouse monoclonals for estrogen and progesterone receptor evaluation in breast cancer by immunohistochemistry"; Pathology Research and Practice; vol. 204; No. 9; pp. 655-662 (Sep. 2008).
Saito et al.; "Drug delivery strategy utilizing conjugation via reversible disulfide linkages: role and site of cellular reducing activities"; Advanced Drug Delivery Reviews; vol. 55; pp. 199-215 (2003).
Schroff et al; "Human anti-murine immunoglobulin responses in patients receiving monoclonal antibody therapy"; Cancer Research; vol. 45; pp. 879-885 (Feb. 1985).
Senter and Springer; "Selective activation of anticancer prodrugs by monoclonal antibody-enzyme conjugates"; Advanced Drug Delivery Reviews; vol. 53; pp. 247-264 (2001).
Shawler et al; "Human immune response to multiple injections of murine monoclonal IgG1"; The Journal of Immunology; vol. 135; No. 2; pp. 1530-1535 (Aug. 1985).
Spieker-Polet et al; "Rabbit monoclonal antibodies: generating a fusion partner to produce rabbit-rabbit hybidomas"; Proc. Natl. Acad. Sci.; vol. 92; pp. 9348-9352 (Sep. 1995).
Takkinen et al; "An active single-chain antibody containing a cellulase linker domain is secreted by *Escherichia coli*"; Protein Engineering; vol. 4; No. 7; pp. 837-841 (1991).
Taub et al.; "A monoclonal antibody against the platelet fibrinogen receptor contains a sequence that mimics a receptor recognition domain in fibrinogen"; The Journal of Biological Chemistry; vol. 264; No. 1; pp. 259-265 (Jan. 5, 1989).
Trail et al.; "Monoclonal antibody drug immunoconjugates for targeted treatment of cancer"; Cancer Immunol. Immunother; vol. 52; pp. 328-337 (2003).
Vallette et al; "Construction of; mutant and chimeric genes using the polymerase chain reaction"; Nucleic Acids Research; vol. 17; No. 2; pp. 723-733 (1989).
Ward et al; "Binding activities of a repertoire of single immunoglobulin variable domains secreted form *Escherichia coli*"; Letters to Nature; vol. 341; pp. 544-546 (Oct. 12, 1989).

(56) References Cited

OTHER PUBLICATIONS

Wells et al; "Cassette mutagenesis: an efficient method for generation of multiple mutations at defined sites"; Gene; vol. 34; pp. 315-323 (1985).

* cited by examiner

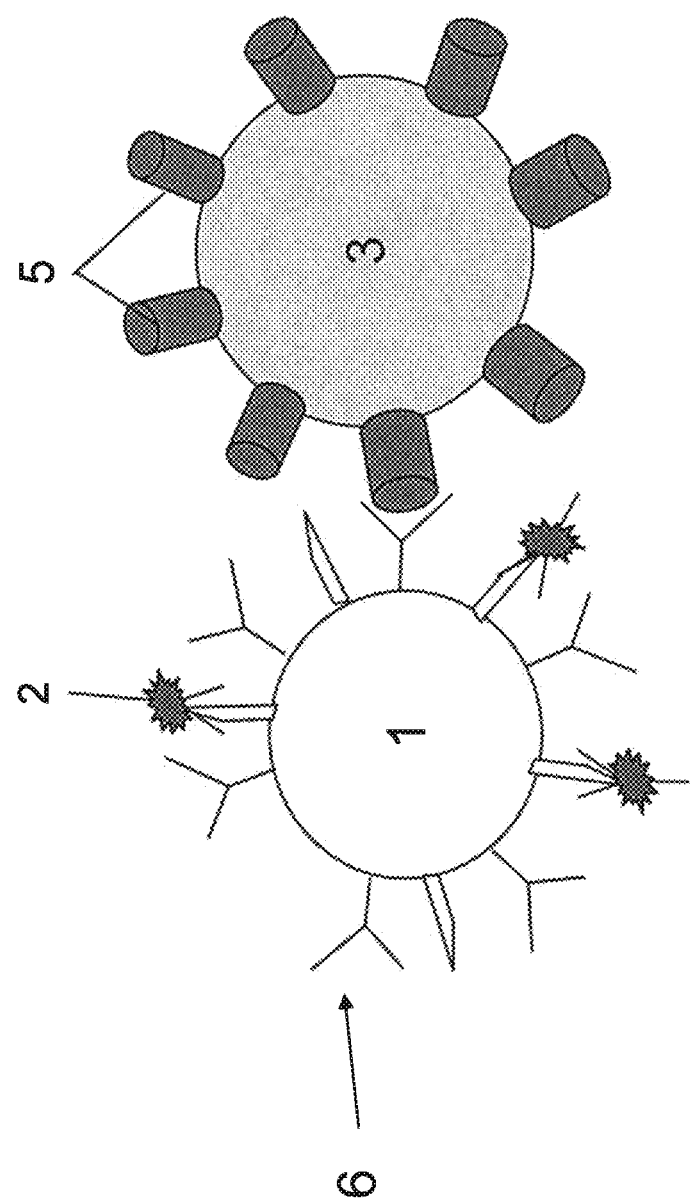

HUMANIZATION OF RABBIT ANTIBODIES USING A UNIVERSAL ANTIBODY FRAMEWORK

RELATED INFORMATION

The present application is a divisional application of U.S. application Ser. No. 14/179,141 filed Feb. 12, 2014 (now allowed), which is a divisional application of U.S. application Ser. No. 13/616,214 filed Sep. 14, 2012 (now U.S. Pat. No. 8,937,162), which is a divisional application of U.S. application Ser. No. 13/000,309 filed Dec. 20, 2010 (now U.S. Pat. No. 8,293,235), which is a 371 national stage application of International Application No. PCT/CH2009/000222 filed Jun. 25, 2009, which claims priority to U.S. Application Ser. No. 61/075,697 filed on Jun. 25, 2008, and further claims priority to U.S. Application Ser. Nos. 61/155,041 and 61/155,105 filed on Feb. 24, 2009.

BACKGROUND OF THE INVENTION

Monoclonal antibodies, their conjugates and derivatives are hugely commercially important as therapeutic and diagnostic agents. Non-human antibodies elicit a strong immune response in patients, usually following a single low dose injection (Schroff, 1985 Cancer Res 45:879-85, Shawler. J Immunol 1985 135:1530-5; Dillman, Cancer Biother 1994 9:17-28). Accordingly, several methods for reducing the immunogenicity of murine and other rodent antibodies as well as technologies to make fully human antibodies using e.g. transgenic mice or phage display were developed. Chimeric antibodies were engineered, which combine rodent variable regions with human constant regions (e.g., Boulianne Nature 1984 312:643-6) reduced immunogenicity problems considerably (e.g., LoBuglio, Proc Natl Acad Sci 1989 86:4220-4; Clark, Immunol Today 2000 21:397-402). Humanized antibodies were also engineered, in which the rodent sequence of the variable region itself is engineered to be as close to a human sequence as possible while preserving at least the original CDRs, or where the CDRs form the rodent antibody were grafted into framework of a human antibody (e.g., Riechmann, Nature 1988 332:323-7; U.S. Pat. No. 5,693,761). Rabbit polyclonal antibodies are widely used for biological assays such as ELISAs or Western blots. Polyclonal rabbit antibodies are oftentimes favored over polyclonal rodent antibodies because of their usually much higher affinity. Furthermore, rabbit oftentimes are able to elicit good antibody responses to antigens that are poorly immunogenic in mice and/or which give not rise to good binders when used in phage display. Due to these well-known advantages of rabbit antibodies, they would be ideal to be used in the discovery and development of therapeutic antibodies. The reason that this is not commonly done is mainly due to technical challenges in the generation of monoclonal rabbit antibodies. Since myeloma-like tumors are unknown in rabbits, the conventional hybridoma technology to generate monoclonal antibodies is not applicable to rabbit antibodies. Pioneering work in providing fusion cell line partners for rabbit antibody-expressing cells has been done by Knight and colleagues (Spieker-Polet et al., PNAS 1995, 92:9348-52) and an improved fusion partner cell line has been described by Pytela et al. in 2005 (see e.g. U.S. Pat. No. 7,429,487). This technology, however, is not wildly spread since the corresponding know-how is basically controlled by a single research group. Alternative methods for the generation of monoclonal antibodies that involve the cloning of antibodies from selected antibody-expressing cells via RT-PCR are described in the literature, but have never been successfully reported for rabbit antibodies.

Rabbit antibodies, like mouse antibodies are expected to elicit strong immune responses if used for human therapy, thus, rabbit antibodies need to be humanized before they can be used clinically. However, the methods that are used to make humanized rodent antibodies cannot easily be extrapolated for rabbit antibodies due to structural differences between rabbit and mouse and, respectively, between rabbit and human antibodies. For example, the light chain CDR3 (CDRL3) is often much longer than previously known CDRL3s from human or mouse antibodies.

There are few rabbit antibody humanization approaches described in the prior art which are, however, no classical grafting approach in which the CDRs of a non-human donor are transplanted on a human acceptor antibody. WO 04/016740 describes a so-called "resurfacing" strategy. The goal of a "resurfacing" strategy is to remodel the solvent-accessible residues of the non-human framework such that they become more human-like. Similar humanization techniques for rabbit antibodies as described in WO 04/016740 are known in the art. Both WO08/144757 and WO05/016950 discloses methods for humanizing a rabbit monoclonal antibody which involve the comparison of amino acid sequences of a parent rabbit antibody to the amino acid sequences of a similar human antibody. Subsequently, the amino acid sequence of the parent rabbit antibody is altered such that its framework regions are more similar in sequence to the equivalent framework regions of the similar human antibody. In order to gain good binding capacities, laborious development efforts need to be made for each immunobinder individually.

A potential problem of the above-described approaches is that not a human framework is used, but the rabbit framework is engineered such that it looks more human-like. Such approach carries the risk that amino acid stretches that are buried in the core of the protein still might comprise immunogenic T cell epitopes.

To date, the applicants have not identified a rabbit antibody, which was humanized by applying state-of-the-art grafting approaches. This might be explained by fact that rabbit CDRs may be quite different from human or rodent CDRs. As known in the art, many rabbit VH chains have extra paired cysteines relative to the murine and human counterparts. In addition to the conserved disulfide bridge formed between cys22 and cys92, there is also a cys21-cys79 bridge as well as an interCDR S—S bridge formed between the last residue of CDRH1 and the first residue of CDR H2 in some rabbit chains. Besides, pairs of cysteine residues are often found in the CDR-L3. Moreover, many rabbit antibody CDRs do not belong to any previously known canonical structure. In particular the CDR-L3 is often much longer than the CDR-L3 of a human or murine counterpart.

Hence, the grafting of non-human CDRs antibodies into a human framework is a major protein engineering task. The transfer of antigen binding loops from a naturally evolved framework to a different artificially selected human framework must be performed so that native loop conformations are retained for antigen binding. Often antigen binding affinity is greatly reduced or abolished after loop grafting. The use of carefully selected human frameworks in grafting the antigen binding loops maximizes the probability of retaining binding affinity in the humanized molecule (Roguzka et al 1996). Although the many grafting experiments available in the literature provide a rough guide for CDR grafting, it is not possible to generalize a pattern. Typical problems consist in losing the specificity, stability or producibility after grafting the CDR loops.

Accordingly, there is an urgent need for improved methods for reliably and rapidly humanizing rabbit antibodies for use as therapeutic and diagnostic agents. Furthermore, there is a need for human acceptor frameworks for reliably humanizing rabbit antibodies, providing functional antibodies and/or antibody fragments with drug-like biophysical properties.

SUMMARY OF THE INVENTION

It has surprisingly been found that a highly soluble and stable human antibody framework identified by a Quality Control (QC) assay (as disclosed in WO 0148017 and in Auf der Maur et al (2001), FEBS Lett 508, p. 407-412) is particularly suitable for accommodating CDRs from other non-human animal species, for example, rabbit CDRs. Accordingly, in a first aspect, the invention provides the light and heavy chain variable regions of a particular human antibody (the so called, "FW 1.4" antibody) which is especially suitable as universal acceptor for CDRs from a variety of antibodies, in particular from rabbit antibodies, of different binding specificities, independent of whether a disulfide bridge is present in a CDR or not. Furthermore, the present invention provides two mutant sequences of said particular human antibody framework, namely rFW1.4 and rFW1.4 (V2), both being frameworks particularly suitable as universal acceptor frameworks for the grafting of rabbit CDRs. In another aspect, the invention provides a motif of framework residues which renders a human framework suitable for accommodating CDRs from other non-human animal species, in particular rabbit CDRs.

Humanized immunobinders generated by the grafting of rabbit CDRs into these highly compatible variable light and heavy chain frameworks consistently and reliably retain the spatial orientation of the rabbit antibodies from which the donor CDRs are derived. Therefore, no structurally relevant positions of the donor immunobinder need to be introduced into the acceptor framework. Due to these advantages, high-throughput humanization of rabbit antibodies with no or little optimization of the binding capacities can be achieved.

Accordingly, in another aspect, the invention provides methods for grafting rabbit and other non-human CDRs, into the soluble and stable light chain and/or heavy chain human antibody framework sequences disclosed herein, thereby generating humanized antibodies with superior biophysical properties. In particular, immunobinders generated by the methods of the invention exhibit superior functional properties such as solubility and stability.

BRIEF DESCRIPTION OF THE DRAWINGS

FIG. 2 schematically shows a B-cell 1 labeled with a fluorescent antibody 2 interacting with a target-expressing cell 3 stained with an intracellular dye 4. Target of choice: 5; BCR: 6.

FIG. 3A: Lymphocytes are gated according to forward and side scatter. FIG. 3B: Among them, IgG+ IgM− cells (probably memory B cells) are selected (red gate). FIG. 3C: Cells double-stained with ESBA903-PE and ESBA903-PerCP (green gate) are expected to encode high affinity IgGs against ESBA903. Cells showing the brightest fluorescence (pink gate) were sorted in 96-well plates.

DETAILED DESCRIPTION OF THE INVENTION

Definitions

Figure 1:
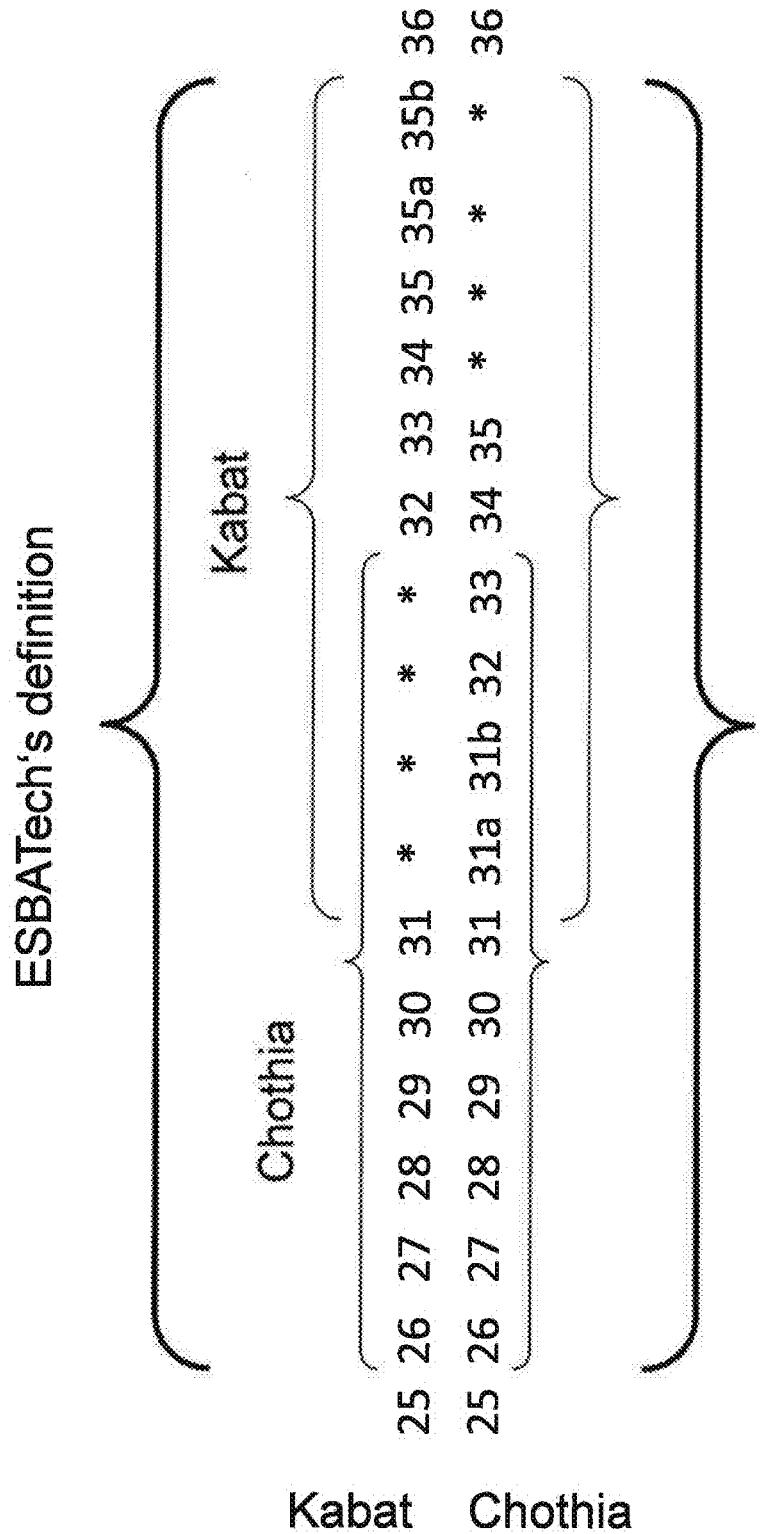
FIG. 1 depicts the CDR H1 definition used herein for grafting antigen binding sites from rabbit monoclonal antibodies into the highly soluble and stable human antibody frameworks.

In order that the present invention may be more readily understood, certain terms will be defined as follows. Additional definitions are set forth throughout the detailed description.

The term "antibody" refers to whole antibodies and any antigen binding fragment. The term "antigen binding polypeptide" and "immunobinder" are used simultaneously herein. An "antibody" refers to a protein, optionally glycosylated, comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion") refers to one or more fragments of an antibody that retain the ability to specifically bind to an antigen (e.g., TNF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

The term "immunobinder" refers to a molecule that contains all or a part of the antigen binding site of an antibody, e.g. all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H$1 domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the $V_H$ and $C_H$1 domains; (v) a Fv fragment consisting of the $V_L$ and $V_H$ domains of a single arm of an antibody, (vi) a single domain antibody such as a Dab fragment (Ward et al., (1989) *Nature* 341:544-546), which consists of a $V_H$ or $V_L$ domain, a Camelid (see Hamers-Casterman, et al., Nature 363:446-448 (1993), and Dumoulin, et al., Protein Science 11:500-515 (2002)) or a Shark antibody (e.g., shark Ig-NARs Nanobodies®; and (vii) a nanobody, a heavy chain variable region containing a single variable domain and two constant domains.

The term "single chain antibody", "single chain Fv" or "scFv" is refers to a molecule comprising an antibody heavy chain variable domain (or region; $V_H$) and an antibody light chain variable domain (or region; $V_L$) connected by a linker. Such scFv molecules can have the general structures: NH$_2$-$V_L$-linker-$V_H$-COOH or NH$_2$-$V_H$-linker-$V_L$-COOH. A suitable state of the art linker consists of repeated GGGGS (SEQ ID NO: 26) amino acid sequences or variants thereof. In a preferred embodiment of the present invention a (GGGGS)$_4$ linker of the amino acid sequence set forth in SEQ ID NO: 8 is used, but variants of 1-3 repeats are also possible (Holliger et al. (1993), Proc. Natl. Acad. Sci. USA 90:6444-6448). Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is stability (e.g., thermal stability). In another embodiment, the functional property is solubility (e.g., under cellular conditions). In yet another embodiment, the functional property is aggregation behavior. In still another embodiment, the functional property is protein expression (e.g., in a prokaryotic cell). In yet another embodiment the functional property is refolding behavior following inclusion body solubilization in a manufacturing process. In certain embodiments, the functional property is not an improvement in antigen binding affinity. In another preferred embodiment, the improvement of one or more functional properties has no substantial effect on the binding affinity of the immunobinder.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the residue positions (Kabat numbering) starting with position 26 and ending prior to position 36. This definition is basically a fusion of CDR H1 as differently defined by Kabat and Chotia (see also FIG. 1 for illustration).

The term "antibody framework" as used herein refers to the part of the variable domain, either VL or VH, which serves as a scaffold for the antigen binding loops (CDRs) of this variable domain. In essence it is the variable domain without the CDRs.

The term "epitope" or "antigenic determinant" refers to a site on an antigen to which an immunoglobulin or antibody specifically binds (e.g., a specific site on the TNF molecule). An epitope typically includes at least 3, 4, 5, 6, 7, 8, 9, 10, 11, 12, 13, 14 or 15 consecutive or non-consecutive amino acids in a unique spatial conformation. See, e.g., *Epitope Mapping Protocols in Methods in Molecular Biology*, Vol. 66, G. E. Morris, Ed. (1996).

The terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower.

The term "$K_D$" or "Kd" refers to the dissociation equilibrium constant of a particular antibody-antigen interaction. Typically, the antibodies of the invention bind to TNF with a dissociation equilibrium constant ($K_D$) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

The term "nucleic acid molecule," as used herein refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector," refers to a nucleic acid molecule capable of transporting another nucleic acid to which it has been linked. In one embodiment, the vector is a "plasmid," which refers to a circular double stranded DNA loop into which additional DNA segments may be ligated. In another embodiment, the vector is a viral vector, wherein additional DNA segments may be ligated into the viral genome. The vectors disclosed herein can be capable of autonomous replication in a host cell into which they are introduced (e.g., bacterial vectors having a bacterial origin of replication and episomal mammalian vectors) or can be can be integrated into the genome of a host cell upon introduction into the host cell, and thereby are replicated along with the host genome (e.g., non-episomal mammalian vectors).

The term "host cell" refers to a cell into which and expression vector has been introduced. Host cells include bacterial, microbial, plant or animal cells, preferably, *Escherichia coli, Bacillus subtilis; Saccharomyces cerevisiae, Pichia pastoris*, CHO (Chinese Hamster Ovary lines) or NS0 cells.

The term "lagomorphs" refers to members of the taxonomic order Lagomorpha, comprising the families Leporidae (e.g. hares and rabbits), and the Ochotonidae (pikas). In a most preferred embodiment, the lagomorphs is a rabbit. The term "rabbit" as used herein refers to an animal belonging to the family of the leporidae.

As used herein, "identity" refers to the sequence matching between two polypeptides, molecules or between two nucleic acids. When a position in both of the two compared sequences is occupied by the same base or amino acid monomer subunit (for instance, if a position in each of two polypeptides is occupied by a lysine), then the respective molecules are identical at that position. The "percentage identity" between two sequences is a function of the number of identical positions shared by the sequences, taking into account the number of gaps, and the length of each gap, which need to be introduced for optimal alignment of the two sequences. Generally, a comparison is made when two sequences are aligned to give maximum identity. Such alignment can be provided using, for instance, the method of the Needleman and Wunsch (J. Mol. Biol. (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending of the specific embodiment, selected definitions, embodiments or ranges may not apply.

If not otherwise stated, the amino acid positions are indicated according to the AHo numbering scheme. The AHo numbering system is described further in Honegger, A. and Pluckthun, A. (2001) *J Mol. Biol.* 309:657-670). Alternatively, the Kabat numbering system as described further in Kabat et al. (Kabat, E. A., et al. (1991) Sequences of Proteins of Immunological Interest, Fifth Edition, U.S. Department of Health and Human Services, NIH Publication No. 91-3242) may be used. Conversion tables for the two different numbering systems used to identify amino acid residue positions in antibody heavy and light chain variable regions are provided in A. Honegger, J. Mol. Biol. 309 (2001) 657-670.

In a first aspect, the present invention provides a universal acceptor framework for the grafting of CDRs from other animal species, for example, from rabbit. It has previously been described that antibodies or antibody derivatives comprising the human frameworks identified in the so called "Quality Control" screen (WO0148017) are characterised by a generally high stability and/or solubility. Although the human single-chain framework FW1.4 (a combination of SEQ ID NO: 1 (named a43 in WO03/097697) and SEQ ID NO: 2 (named KI27 in WO03/097697)) clearly underperformed in the Quality Control assay, it was surprisingly found that it has a high intrinsic thermodynamic stability and is well producible, also in combination with a variety of different CDRs. The stability of this molecule can be attributed mostly to its framework regions. It has further been shown that FW1.4 is in essence highly compatible with the antigen-binding sites of rabbit antibodies. Therefore, the FW1.4 represents a suitable scaffold to construct stable humanized scFv antibody fragments derived from grafting of rabbit loops. Thus, in one aspect, the invention provides an immunobinder acceptor framework, comprising a VH sequence having at least 90% identity to SEQ ID No. 1 and/or a VL sequence having at least 85% identity to SEQ ID No. 2, more preferably comprising the sequence of FW1.4 (SEQ ID NO: 3) for the grafting of rabbit CDRs, or a sequence having at least 60%, more preferably at least 65%, 70%, 75%, 80%, 85%, 90%, 95%, identity to SEQ ID NO: 3.

Moreover, it was found that FW1.4 could be optimized by substituting several residue positions in the heavy chain of FW1.4 and/or by substituting 1 position in the light chain of FW1.4. Thereby, it was surprisingly found that loop conformation of a large variety of rabbit CDRs in the VH could be fully maintained, largely independent of the sequence of the donor framework. Said residues in the heavy chain as well as the 1 position in the light chain of FW1.4 are conserved in rabbit antibodies. The consensus residue for the positions in the heavy chain as well as the one position in the light chain was deduced from the rabbit repertoire and introduced into the sequence of the human acceptor framework.

As a result, the modified framework 1.4 (hereinafter referred to as rFW1.4) is compatible with virtually any rabbit CDRs. Moreover, rFW1.4 containing different rabbit CDRs is well expressed and good produced contrary to the rabbit wild type single chains and still almost fully retains the affinity of the original donor rabbit antibodies.

Thus, the present invention provides the variable heavy chain framework of SEQ ID No. 1, further comprising one or more amino acid residues that generally support conformation of CDRs derived from a rabbit immunobinder. In particular, said residues are present at one or more amino acid positions selected from the group consisting of 24H, 25H, 56H, 82H, 84H, 89H and 108H (AHo numbering). These positions are prove to affect CDR conformation and are therefore contemplated for mutation to accommodate donor CDRs. Preferably, said one or more residues are selected from the group consisting of: Threonine (T) at position 24, Valine (V) at position 25, Glycine or Alanine (G or A) at position 56, Lysine (K) at position 82, Threonine (T) at position 84, Valine (V) at position 89 and Arginine (R) at position 108 (AHo numbering). Preferably, at least three, more preferably, four, five, six and most preferably all seven residues are present. Surprisingly, it has been found that the presence of the mentioned residues improves the stability of the immunobinder.

In a preferred embodiment, the invention provides an immunobinder acceptor framework comprising a VH having at least 50%, more preferably at least 55%, 60%, 65%, 70%, 75%, 80%, 85%, 90%, 95% and even more preferably 100% identity to SEQ ID No. 4, with the provisio that at least one, more preferably at least three, more preferably, four, five, six and most preferably seven residues of the group consisting of threonine (T) at position 24, valine (V) at position 25, alanine (A) or glycine (G) at position 56, threonine (T) at position 84, lysine (K) at position 82, valine (V) at position 89 and arginine (R) at position 108 (AHo numbering) are present. In a preferred embodiment, the immunobinder acceptor framework is an immunobinder acceptor framework for rabbit CDRs.

In a preferred embodiment, said variable heavy chain framework is or comprises SEQ ID No. 4 or SEQ ID No. 6. Both of said variable heavy chain frameworks may for example be combined with any suitable light chain framework.

Accordingly, the present invention provides an immunobinder acceptor framework comprising (i) a variable heavy chain framework having at least 70% identity, preferably at least 75%, 80%, 85%, 90%, more preferably at least 95% identity, to SEQ ID No. 4; and/or (ii) a variable light chain framework having at least 70% identity, preferably at least 75%, 80%, 85%, 90%, more preferably at least 95% identity, to SEQ ID No. 2.

In a much preferred embodiment, the variable heavy chain framework comprises threonine (T) at position 24, glycine (G) at position 56, threonine (T) at position 84, valine (V) at position 89 and arginine (R) at position 108 (AHo numbering).

In a preferred embodiment, the variable light chain comprises Threonine (T) at position 87 (AHo numbering).

In a preferred embodiment, said immunobinder acceptor framework comprises (i) a variable heavy chain framework selected from the group consisting of SEQ ID No. 1, SEQ ID No. 4 and SEQ ID No. 6; and/or (ii) a variable light chain framework of SEQ ID No. 2 or SEQ ID No. 9.

In a preferred embodiment, the variable heavy chain framework is linked to a variable light chain framework via a linker. The linker may be any suitable linker, for example a linker comprising 1 to 4 repeats of the sequence GGGGS (SEQ ID NO: 26), preferably a (GGGGS)$_4$ peptide (SEQ ID No. 8), or a linker as disclosed in Alfthan et al. (1995) Protein Eng. 8:725-731.

In another preferred embodiment, the immunobinder acceptor framework is a sequence having at least 70%, 75%, 80%, 85%, 90% more preferably at least 95% identity, to SEQ ID No. 5, whereas the sequence, preferably, is not SEQ ID No. 3. More preferably, the immunobinder acceptor framework comprises or is SEQ ID No. 5.

In another preferred embodiment, the immunobinder acceptor framework is a sequence having at least 70%, 75%, 80%, 85%, 90%, more preferably at least 95% identity, to SEQ ID No. 7, whereas the sequence, preferably, is not SEQ ID No. 3. More preferably, the immunobinder acceptor framework comprises or is SEQ ID No. 7.

Moreover, it was surprisingly found that the presence of the above described amino acid motif renders a framework, preferably a human framework, particularly suitable for the accommodation of CDRs from other non-human animal species, in particular rabbit CDRs. Said motif has no negative impact on the stability of an immunobinder. The CDRs are presented in a conformation similar to their native spatial orientation in the rabbit immunobinder; thus, no structurally relevant positions need to be grafted onto the acceptor framework. Accordingly, the human or humanized immunobinder acceptor framework comprises at least three amino acids, preferably four, five, six and more preferably seven amino acids of the group consisting of threonine (T) at position 24, valine (V) at position 25, alanine (A) or glycine (G) at position 56, lysine (K) at position 82, threonine (T) at position 84, valine (V) at position 89 and arginine (R) at position 108 (AHo numbering).

The immunobinder acceptor frameworks as described herein may comprise solubility enhancing substitution in the heavy chain framework, preferably at positions 12, 103 and 144 (AHo numbering). Preferably, a hydrophobic amino acid is substituted by a more hydrophilic amino acid. Hydrophilic amino acids are e.g. Arginine (R), Asparagine (N), Aspartic acid (D), Glutamine (Q), Glycine (G), Histidine (H), Lysine (K), Serine (S) and Threonine (T). More preferably, the heavy chain framework comprises (a) Serine (S) at position 12; (b) Serine (S) or Threonine (T) at position 103 and/or (c) Serine (S) or Threonine (T) at position 144.

Moreover, stability enhancing amino acids may be present at one or more positions 1, 3, 4, 10, 47, 57, 91 and 103 of the variable light chain framework (AHo numbering). More preferably, the variable light chain framework comprises glutamic acid (E) at position 1, valine (V) at position 3, leucine (L) at position 4, Serine (S) at position 10; Arginine (R) at position 47, Serine (S) at position 57, phenylalanine (F) at position 91 and/or Valine (V) at position 103.

As glutamine (Q) is prone to desamination, in another preferred embodiment, the VH comprises at position 141 a glycine (G). This substitution may improve long-term storage of the protein.

For example, the acceptor frameworks disclosed herein can be used to generate a human or humanized antibody which retains the binding properties of the non-human antibody from which the non-human CDRs are derived. Accordingly, in a preferred embodiment the invention encompasses an immunobinder acceptor framework as disclosed herein, further comprising heavy chain CDR1, CDR2 and CDR3 and/or light chain CDR1, CDR2 and CDR3 from a donor immunobinder, preferably from a mammalian immunobinder, more preferably from a lagomorph immunobinder and most preferably from a rabbit. Thus, in one embodiment, the invention provides an immunobinder specific to a desired antigen comprising (i) variable light chain CDRs of a lagomorph; and
(ii) a human variable heavy chain framework having at least 50% identity to SEQ ID NO. 4.

In one preferred embodiment, there is the provisio that at least one amino acid of the group consisting of threonine (T) at position 24, valine (V) at position 25, alanine (A) or glycine (G) at position 56, threonine (T) at position 84, lysine (K) at position 82, valine (V) at position 89 and arginine (R) at position 108 (AHo numbering) is present in said human variable heavy chain framework sequence.

Preferably, the lagomorph is a rabbit. More preferably, the immunobinder comprises heavy chain CDR1, CDR2 and CDR3 and light chain CDR1, CDR2 and CDR3 from the donor immunobinder.

As known in the art, many rabbit VH chains have extra paired cysteines relative to the murine and human counterparts. In addition to the conserved disulfide bridge formed between cys22 and cys92, there is also a cys21-cys79 bridge as well as an interCDR S—S bridge formed between the last residue of CDRH1 and the first residue of CDR H2 in some rabbit chains. Besides, pairs of cysteine residues in the CDR-L3 are often found. Besides, many rabbit antibody CDRs do not belong to any previously known canonical structure. In particular the CDR-L3 is often much longer than the CDR-L3 of a human or murine counterpart.

As stated before, the grafting of the non-human CDRs onto the frameworks disclosed herein yields a molecule wherein the CDRs are displayed in a proper conformation. If required, the affinity of the immunobinder may be improved by grafting antigen interacting framework residues of the non-human donor immunobinder. These positions may e.g. be identified by (i) identifying the respective germ line progenitor sequence or, alternatively, by using the consensus sequences in case of highly homologous framework sequences;
(ii) generating a sequence alignment of donor variable domain sequences with germ line progenitor sequence or consensus sequence of step (i); and
(iii) identifying differing residues.

Differing residues on the surface of the molecule were in many cases mutated during the affinity generation process in vivo, presumably to generate affinity to the antigen.

In another aspect, the present invention provides an immunobinder which comprises the immunobinder acceptor framework described herein. Said immunobinder may e.g. be a scFv antibody, a full-length immunoglobulin, a Fab fragment, a Dab or a Nanobody.

In a preferred embodiment, the immunobinder is attached to one or more molecules, for example a therapeutic agent such as a cytotoxic agent, a cytokine, a chemokine, a growth factor or other signaling molecule, an imaging agent or a second protein such as a transcriptional activator or a DNA-binding domain.

The immunobinder as disclosed herein may e.g. be used in diagnostic applications, therapeutic application, target validation or gene therapy.

The invention further provides an isolated nucleic acid encoding the immunobinder acceptor framework disclosed herein or the immunobinder(s) as disclosed herein.

In another embodiment, a vector is provided which comprises the nucleic acid disclosed herein.

The nucleic acid or the vector as disclosed herein can e.g. be used in gene therapy.

The invention further encompasses a host cell comprising the vector and/or the nucleic acid disclosed herein.

Moreover, a composition is provided, comprising the immunobinder acceptor framework as disclosed herein, the immunobinder as disclosed herein, the isolated nucleic acid as disclosed herein or the vector as disclosed herein.

The sequences disclosed herein are the following (X residues are CDR insertion sites):

SEQ ID NO.1: variable heavy chain framework of FW1.4 (a43)
EVQLVESGGGLVQPGGSLRLSCAAS(X)$_{n=1-50}$ WVRQAPGKGLEWVS(X)$_{n=1-50}$ RFTISRDNSKNTLYLQMNSLRAEDTAVYYCAK(X)$_{n=1-50}$

WGQGTL VTVSS

SEQ ID NO. 2: variable light chain framework of FW1.4 (KI27)
EIVMTQSPSTLSASVGDRVIITC(X)$_{n=1-50}$ WYQQKPGKAPKLLIY(X)$_{n=1-50}$ GVPSRFSGSGSGAEFTLTISSLQPDDFATYYC(X)$_{n=1-50}$

FGQGTKLT VLG

SEQ ID NO. 3: framework of FW1.4
EIVMTQSPSTLSASVGDRVIITC(X)$_{n=1-50}$

WYQQKPGKAPKLLIY(X)$_{n=1-50}$

GVPSRFSGSGSGAEFTLTISSLQPDDFATYYC(X)$_{n=1-50}$

FGQGTKLTVLGGGGSGGGGSGGGGSGGGGS

EVQLVESGGGLVQPGGSLRLSCAAS(X)$_{n=1-50}$

WVRQAPGKGLEWVS(X)$_{n=1-50}$ RFTISRDNSKNTLYLQMNSLRAEDTA

VYYCAK(X)$_{n=1-50}$ WGQGTLVTVSS

SEQ ID NO. 4: variable heavy chain framework of rFW1.4
EVQLVESGGGLVQPGGSLRLSCTAS(X)$_{n=1-50}$ WVRQAPGKGLEWVG(X)$_{n=1-50}$ RFTISRDTSKNTVYLQMNSLRAEDTAVYYCAR(X)$_{n=1-50}$

WGQGTLV TVSS

SEQ ID NO. 5: framework of rFW1.4
EIVMTQSPSTLSASVGDRVIITC(X)$_{n=1-50}$

WYQQKPGKAPKLLIY(X)$_{n=1-50}$

GVPSRFSGSGSGTEFTLTISSLQPDDFATYYC(X)$_{n=1-50}$

FGQGTKLTVLGGGGSGGGGSGGGGSGGGGSEVQLVESGGGLVQP

GGSLRLSCTAS(X)$_{n=1-50}$ WVRQAPGKGLEWVG(X)$_{n=1-50}$

RFTISRDTSKNTVYLQMNSLRAEDTAVYYCAR(X)$_{n=1-50}$

WGQGTLVTVSS

-continued

SEQ ID NO. 6: variable heavy chain framework of
rFW1.4(V2)
EVQLVESGGGLVQPGGSLRLSCTVS(X)$_{n=1-50}$ WVRQAPGKGLEWVG(X)$_{n=1-50}$ RFTISKDTSKNTVYLQMNSLRAEDTAVYYCAR(X)$_{n=1-50}$

WGQGTLVTVSS

SEQ ID NO. 7: framework of rFW1.4(V2)
EIVMTQSPSTLSASVGDRVIITC(X)$_{n=1-50}$

WYQQKPGKAPKLLIY(X)$_{n=1-50}$

GVPSRFSGSGSGTEFTLTISSLQPDDFATYYC(X)$_{n=1-50}$

FGQGTKLTVLGGGGSGGGGSGGGGSGGGGS

EVQLVESGGGLVQPGGSLRLSCTVS(X)$_{n=1-50}$

WVRQAPGKGLEWVG(X)$_{n=1-50}$ RFTISKDTSKNTVYLQMNSLR

AEDTAVYYCAR(X)$_{n=1-50}$ WGQGTLVTVSS

SEQ ID NO. 8: linker
GGGGSGGGGSGGGGSGGGGS

SEQ ID NO. 9: substituted variable light chain
framework of FW1.4
EIVMTQSPSTLSASVGDRVIITC(X)$_{n=1-50}$ WYQQKPGKAPKLLIY(X)$_{n=1-50}$ GVPSRFSGSGSGTEFTLTISSLQPDDFATYYC(X)$_{n=1-50}$

FGQGTKLTVLG

In another aspect, the invention provides methods for the humanization of non-human antibodies by grafting CDRs of non-human donor antibodies onto stable and soluble antibody frameworks. In a particularly preferred embodiment, the CDRs stem from rabbit antibodies and the frameworks are those described above.

A general method for grafting CDRs into human acceptor frameworks has been disclosed by Winter in U.S. Pat. No. 5,225,539 and by Queen et al. in WO9007861A1, which are hereby incorporated by reference in their entirety. The general strategy for grafting CDRs from rabbit monoclonal antibodies onto selected frameworks is related to that of Winter et al. and Queen et al., but diverges in certain key respects. In particular, the methods of the invention diverge from the typical Winter and Queen methodology known in the art in that the human antibody frameworks as disclosed herein are particularly suitable as universal acceptors for human or non-human donor antibodies. Thus, unlike the general method of Winter and Queen, the framework sequence used for the humanization methods of the invention is not necessarily the framework sequence which exhibits the greatest sequence similarity to the sequence of the non-human (e.g., rabbit) antibody from which the donor CDRs are derived. In addition, framework residue grafting from the donor sequence to support CDR conformation is not required. At most, antigen binding amino acids located in the framework or other mutations that occurred during somatic hypermutation may be introduced.

Particular details of the grafting methods to generate humanized rabbit-derived antibodies with high solubility and stability are described below.

Accordingly, the invention provides a method of humanizing a rabbit CDR donor immunobinder which comprises heavy chain CDR1, CDR2 and CDR3 sequences and/or light chain CDR1, CDR2 and CDR3 sequences. The method comprises the steps of:

(i) grafting onto the heavy chain at least one, preferably two, more preferably three CDRs of the group consisting of CDR1, CDR2 and CDR3 sequences into a human heavy chain acceptor framework having at least 50%, preferably at least 55%, 60%, 65%, 70%, 75%, 80%, 85%, 90%, more preferably at least 95% identity to SEQ ID NO:1; and/or (ii) grafting onto the light chain at least one, preferably two, more preferably three CDRs of the group consisting of CDR1, CDR2 and CDR3 sequences into a human light chain acceptor framework, the human light chain framework having at least 50%, preferably at least 55%, 60%, 65%, 70%, 75%, 80%, 85%, 90%, more preferably at least 95% identity to SEQ ID NO:2.

In a preferred embodiment, the variable chain acceptor framework comprises (i) a human heavy chain framework comprising a framework amino acid sequence selected from the group consisting of SEQ ID NO:1, SEQ ID NO:4 and SEQ ID NO:6 and (ii) a human light chain framework comprising the framework amino acid sequence of SEQ ID NO:2 or SEQ ID NO:9.

In a much preferred embodiment, the method comprises the step of (i) grafting the heavy chain CDR1, CDR2 and CDR3 sequences into the heavy chain and (ii) grafting the light chain CDR1, CDR2 and CDR3 sequences into the light chain of an immunobinder having at least 75%, 80%, 85%, 90%, more preferably at least 95% identity to SEQ ID No. 3, SEQ ID No. 5 or SEQ ID No. 7. More preferably, the immunobinder is or comprises SEQ ID No. 3, SEQ ID No. 5 or SEQ ID No. 7.

In another embodiment, in order to improve antigen binding, the method may further comprise the step of substituting acceptor framework residues by donor residues which are involved in antigen binding.

In exemplary embodiments of the methods of the invention, the amino acid sequence of the CDR donor antibody is first identified and the sequences aligned using conventional sequence alignment tools (e.g., Needleman-Wunsch algorithm and Blossum matrices). The introduction of gaps and nomenclature of residue positions may be done using a conventional antibody numbering system. For example, the AHo numbering system for immunoglobulin variable domains may be used. The Kabat numbering scheme may also be applied since it is the most widely adopted standard for numbering the residues in an antibody. Kabat numbering may e.g. be assigned using the SUBIM program. This program analyses variable regions of an antibody sequence and numbers the sequence according to the system established by Kabat and co-workers (Deret et al 1995). The definition of framework and CDR regions is generally done following the Kabat definition which is based on sequence variability and is the most commonly used. However, for CDR-H1, the designation is preferably a combination of the definitions of Kabat's, mean contact data generated by analysis of contacts between antibody and antigen of a subset of 3D complex structures (MacCallum et al., 1996) and Chotia's which is based on the location of the structural loop regions (see also FIG. 1). Conversion tables for the two different numbering systems used to identify amino acid residue positions in antibody heavy and light chain variable regions are provided in A. Honegger, J. Mol. Biol. 309 (2001) 657-670. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242). The AHo numbering system is described further in Honegger, A. and Pluckthun, A. (2001) *J Mol. Biol.* 309:657-670).

The variable domains of the rabbit monoclonal antibodies may e.g. be classified into corresponding human sub-groups using e.g. an EXCEL implementation of sequence analysis algorithms and classification methods based on analysis of the human antibody repertoire (Knappik et al., 2000, *J Mol Biol*. February 11; 296(1):57-86).

CDR conformations may be assigned to the donor antigen binding regions, subsequently residue positions required to maintain the different canonical structures can also be identified. The CDR canonical structures for five of the six antibody hypervariable regions of rabbit antibodies (L1, L2, L3, H1 and H2) are determined using Chothia's (1989) definition.

In a preferred embodiment, the CDRs are generated, identified and isolated according to the following method: B-cells, preferably rabbit B-cells, are incubated with (i) target antigens (preferably purified) or (ii) with cells expressing the target antigen on their surface.

In case (ii), said cells expressing the target antigen may e.g. be mammalian cells, preferably CHO or HEK293 cells, yeast cells, preferably yeast spheroblasts, or bacterial cells which naturally express the target of choice or are transformed to express the target protein on their surface. Upon expression, the target antigen may be expressed on the cell surface either integrated or attached to the cell membrane. The cells may e.g. be cultivated as isolated strains in cell culture or be isolated from their natural environment, e.g. a tissue, an organ or an organism.

Providing the target antigen expressed on the surface of cells, i.e. case (ii), is especially preferred for transmembrane proteins, even more preferably for multi-membrane-spanning proteins, such as GPCRs (G protein-coupled receptors) or ion channels or any other protein of which the native conformation is difficult to maintain upon recombinant expression and purification. Traditional immunization with the recombinant protein is in these cases inadvisable or impossible due to loss of native conformation of integral membrane proteins/complexes during the purification process or due to insufficient amounts of pure protein. In a preferred embodiment of the invention, a mammal, more preferably a rabbit, is immunized with DNA instead of recombinant protein e.g. by a DNA vaccination protocol as disclosed in WO/2004/087216. DNA vaccination induces a rapid immune response against a native antigen. Since no recombinant protein is needed, this technology is on one hand very cost-effective, on the other hand, and more importantly, this method allows for native expression of integral membrane complexes and/or multi-membrane-spanning membrane proteins. The B-cells may be isolated from said immunized mammal, preferably of said rabbit, or alternatively be naive B-cells.

In a subsequent step of said method B-cells, preferably memory B-cells, are isolated from lymphatic organs of the immunized animal (such as spleen or lymph nodes), preferably of immunized rabbits. The B-cells are incubated in a mixture with either cells expressing the antigen on their surface or with fluorescence-labeled soluble antigen. B-cells that express target specific antibodies on their surface and consequently bind to the target antigen or to the target antigen expressed on the cell surface are isolated. In a much preferred embodiment, the B-cells and/or the target cells are stained to allow for isolation via flow cytometry based sorting of B-cell/target cell or B-cell/antigen complexes. Flow cytometry normally measures the fluorescence emitted by single cells when they cross a laser beam. However, some researchers have already used cytometers to investigate cell-cell interactions, for example adhesion mediated by cadherins (Panorchan et al, 2006, J. Cell Science, 119, 66-74; Leong et Hibma, 2005, J. Immunol. Methods, 302, 116-124) or integrins (Gawaz et al, 1991, J. Clin. Invest, 88, 1128-1134). Thus, in case (ii), cells expressing the target of choice are stained with an intracellular fluorescent dye (for example calcein). B-cells are stained with fluorescent antibodies binding to cell surface specific markers. Thus, bi-color "events" may be selected, consisting in two cells adhering to each other through B-cell receptor-target interactions (see FIG. 2).

As IgG have generally a higher affinity as IgMs, preferably, positive B-cells expressing IgG but not IgM on their surface (which is characteristic for memory B-cells) are selected. For said purpose, multicolor staining is preferably used, where antibodies specific for IgG and IgM are differentially labeled, e.g. with APC and FITC, respectively.

In one particular embodiment, a read-out for B-cell sorting can also select for the ability of this interaction to functionally block/activate receptor signaling. For example, B-cells could be incubated with cells that functionally express a GPCR (G protein-coupled receptor). An agonist that signals through a GPCR can be added to the mixture to induce GPCR mediated Ca2+ efflux from the endoplasmic reticulum. In case an antibody presented on a B-cell would functionally block agonist signaling, Ca2+ efflux would consequently also be blocked by this cell-cell interaction. Ca2+ efflux can be quantitatively measured by flow-cytometry. Therefore, only B-cell/target cell conglomerates that either show increase or decrease in Ca2+ efflux would be sorted.

The selection step is followed by the cultivation of the B-cells under suitable conditions so that antibodies are secreted into the culture medium. The produced antibodies are monoclonal antibodies. The cultivation may involve the use of a helper cell line, such as a thymoma helper cell line (e.g. EL4-B5, see Zubler et al, 1985, J. Immunol., 134(6): 3662-3668). Preferably, a validation step is performed testing the generated antibodies for specific binding to the target, e.g. for excluding antibodies which are directed against a protein being expressed on the cell surface other than the target protein. For example, CELISA, i.e. a modified enzyme-linked immunosorbent assay (ELISA), where coating step is performed with entire cells, is suitable for said purpose. Said method allows for the evaluation of the selectivity and the ability of antibodies to compete with the ligand.

The antibodies generated in the above mentioned step are then analyzed to identify the CDRs of said antibodies. This may involve steps such as purifying the antibodies, elucidating their amino acid sequence and/or nucleic acid sequence.

Finally, the CDRs may then be grafted onto acceptor frameworks e.g. by gene synthesis with the oligo extension method, preferably onto the acceptor frameworks described above. In one embodiment, the art recognized process of CDR grafting can be used to transfer donor CDRs into acceptor frameworks. In most cases, all three CDRs from the heavy chain are transplanted from the donor antibody to a single acceptor framework and all three CDRs from the light chain are transplanted to a different acceptor framework. It is expected that it should not always be necessary to transplant all the CDRs, as some CDRs may not be involved in binding to antigen, and CDRs with different sequences (and the same length) can have the same folding (and therefore contacts from antigen to the main chain contacts could be retained despite the different sequences). Indeed single domains (Ward et al, 1989, Nature 341, pp. 544-546) or even single CDRs (R. Taub et al, 1989, J. Biol Chem 264, pp. 259-265) can have antigen binding activities alone. However, whether all or only some of the CDRs are transplanted, the intention of CDR grafting is to transplant the same, or much the same antigen binding site, from animal to human antibodies (see, e.g., U.S. Pat. No. 5,225,539 (Winter)).

In another embodiment, the CDRs of the donor antibody can be altered prior to or after their incorporation into the acceptor framework.

Alternatively, characterization of the antibodies would be performed only in their final immunobinder format. For this approach, CDR sequences of antibodies expressed on sorted B-cells are retrieved by RT-PCR from either the cultured sorted B-cells or from single sorted B-cells directly. For said purpose, multiplication of B-cells and/or the validation step described above and/or the analyzation step as described above may not be necessary. Combination of two pools of partially overlapping oligonucleotides in which one oligonucleotide pool is coding for the CDRs and a second pool encodes the framework regions of a suitable immunobinder scaffold would allow to generate a humanized immunobinders in a one-step PCR procedure. Highthroughput sequencing, cloning and production would allow to perform clone selection based on the performance of the purified humanized immunobinders, instead of characterizing secreted IgG in the cell culture supernatant. In a preferred embodiment thereof, the immunobinder is a scFv.

However, grafting of CDRs may result in an impaired affinity of the generated immunobinder to the antigen due to framework residues which are in contact with the antigen. Such interactions may be a result of somatic hypermutation. Therefore, it may still be required to graft such donor framework amino acids onto the framework of the humanized antibody. Amino acid residues from the non-human immunobinder involved in antigen binding may be identified by examination of rabbit monoclonal antibody variable region sequences and structures. Each residue in the CDR donor framework that differs from the germline may be considered as relevant. If the closest germline cannot be established, the sequence can be compared against the subgroup consensus or the consensus of rabbit sequences with a high percentage of similarity. Rare framework residues are considered as possible result of somatic hypermutation and therefore as playing a role in binding.

The antibodies of the invention may be further optimized to show enhanced functional properties, e.g., enhanced solubility and/or stability. In certain embodiments, the antibodies of the invention are optimized according to the "functional consensus" methodology disclosed in PCT Application Serial No. PCT/EP2008/001958, entitled "Sequence Based Engineering and Optimization of Single Chain Antibodies", filed on Mar. 12, 2008, which is incorporated herein by reference.

For example, the immunobinders of the invention can be compared with a database of functionally-selected scFvs is used to identify amino acid residue positions that are either more or less tolerant of variability than the corresponding positions in immunobinder, thereby indicating that such identified residue positions may be suitable for engineering to improve functionality such as stability and/or solubility.

Exemplary framework residue positions for substitution and exemplary framework substitutions are described in PCT Application No. PCT/CH2008/000285, entitled "Methods of Modifying Antibodies, and Modified Antibodies with Improved Functional Properties", filed on Jun. 25, 2008, and PCT Application No. PCT/CH2008/000284, entitled "Sequence Based Engineering and Optimization of Single Chain Antibodies", filed on Jun. 25, 2008. For example, one or more of the following substitutions may be introduced at an amino acid position (AHo numbering is referenced for each of the amino acid position listed below) in the heavy chain variable region of an immunobinder of the invention:

(a) Q or E at amino acid position 1;
(b) Q or E at amino acid position 6;
(c) T, S or A at amino acid position 7, more preferably T or A, even more preferably T;
(d) A, T, P, V or D, more preferably T, P, V or D, at amino acid position 10,
(e) L or V, more preferably L, at amino acid position 12,
(f) V, R, Q, M or K, more preferably V, R, Q or M at amino acid position 13;
(g) R, M, E, Q or K, more preferably R, M, E or Q, even more preferably R or E, at amino acid position 14;
(h) L or V, more preferably L, at amino acid position 19;
(i) R, T, K or N, more preferably R, T or N, even more preferably N, at amino acid position 20;
(j) I, F, L or V, more preferably I, F or L, even more preferably I or L, at amino acid position 21;
(k) R or K, more preferably K, at amino acid position 45;
(l) T, P, V, A or R, more preferably T, P, V or R, even more preferably R, at amino acid position 47;
(m) K, Q, H or E, more preferably K, H or E, even more preferably K, at amino acid position 50;
(n) M or I, more preferably I, at amino acid position 55;
(o) K or R, more preferably K, at amino acid position 77;
(p) A, V, L or I, more preferably A, L or I, even more preferably A, at amino acid position 78;
(q) E, R, T or A, more preferably E, T or A, even more preferably E, at amino acid position 82;
(r) T, S, I or L, more preferably T, S or L, even more preferably T, at amino acid position 86;
(s) D, S, N or G, more preferably D, N or G, even more preferably N, at amino acid position 87;
(t) A, V, L or F, more preferably A, V or F, even more preferably V, at amino acid position 89;
(u) F, S, H, D or Y, more preferably F, S, H or D, at amino acid position 90;
(v) D, Q or E, more preferably D or Q, even more preferably D, at amino acid position 92;
(w) G, N, T or S, more preferably G, N or T, even more preferably G, at amino acid position 95;
(x) T, A, P, F or S, more preferably T, A, P or F, even more preferably F, at amino acid position 98;
(y) R, Q, V, I, M, F, or L, more preferably R, Q, I, M, F or L, even more preferably Y, even more preferably L, at amino acid position 103; and
(z) N, S or A, more preferably N or S, even more preferably N, at amino acid position 107.

Additionally or alternatively, one or more of the following substitutions can be introduced into the light chain variable region of an immunobinder of the invention:

(aa) Q, D, L, E, S, or I, more preferably L, E, S or I, even more preferably L or E, at amino acid position 1;
(bb) S, A, Y, I, P or T, more preferably A, Y, I, P or T, even more preferably P or T at amino acid position 2;
(cc) Q, V, T or I, more preferably V, T or I, even more preferably V or T, at amino acid position 3;
(dd) V, L, I or M, more preferably V or L, at amino acid position 4;
(ee) S, E or P, more preferably S or E, even more preferably S, at amino acid position 7;
(ff) T or I, more preferably I, at amino acid position 10;
(gg) A or V, more preferably A, at amino acid position 11;
(hh) S or Y, more preferably Y, at amino acid position 12;

(ii) T, S or A, more preferably T or S, even more preferably T, at amino acid position 14;
(jj) S or R, more preferably S, at amino acid position 18;
(kk) T or R, more preferably R, at amino acid position 20;
(ll) R or Q, more preferably Q, at amino acid position 24;
(mm) H or Q, more preferably H, at amino acid position 46;
(nn) K, R or I, more preferably R or I, even more preferably R, at amino acid position 47;
(oo) R, Q, K, E, T, or M, more preferably Q, K, E, T or M, at amino acid position 50;
(pp) K, T, S, N, Q or P, more preferably T, S, N, Q or P, at amino acid position 53;
(qq) I or M, more preferably M, at amino acid position 56;
(rr) H, S, F or Y, more preferably H, S or F, at amino acid position 57;
(ss) I, V or T, more preferably V or T, R, even more preferably T, at amino acid position 74;
(tt) R, Q or K, more preferably R or Q, even more preferably R, at amino acid position 82;
(uu) L or F, more preferably F, at amino acid position 91;
(vv) G, D, T or A, more preferably G, D or T, even more preferably T, at amino acid position 92;
(xx) S or N, more preferably N, at amino acid position 94;
(yy) F, Y or S, more preferably Y or S, even more preferably S, at amino acid position 101; and
(zz) D, F, H, E, L, A, T, V, S, G or I, more preferably H, E, L, A, T, V, S, G or I, even more preferably A or V, at amino acid position 103.

In other embodiments, the immunobinders of the invention comprise one or more of the stability enhancing mutations described in U.S. Provisional Application Ser. No. 61/075,692, entitled "Solubility Optimization of Immunobinders", filed on Jun. 25, 2008. In certain preferred embodiments, the immunobinder comprises a solubility enhancing mutation at an amino acid position selected from the group of heavy chain amino acid positions consisting of 12, 103 and 144 (AHo Numbering convention). In one preferred embodiment, the immunobinder comprises one or more substitutions selected from the group consisting of: (a) Serine (S) at heavy chain amino acid position 12; (b) Serine (S) or Threonine (T) at heavy chain amino acid position 103; and (c) Serine (S) or Threonine (T) at heavy chain amino acid position 144. In another embodiment, the immunobinder comprises the following substitutions: (a) Serine (S) at heavy chain amino acid position 12; (b) Serine (S) or Threonine (T) at heavy chain amino acid position 103; and (c) Serine (S) or Threonine (T) at heavy chain amino acid position 144.

In certain preferred embodiments, the immunobinder comprises stability enhancing mutations at a framework residue of the light chain acceptor framework in at least one of positions 1, 3, 4, 10, 47, 57, 91 and 103 of the light chain variable region according to the AHo numbering system. In a preferred embodiment, the light chain acceptor framework comprises one or more substitutions selected from the group consisting of (a) glutamic acid (E) at position 1, (b) valine (V) at position 3, (c) leucine (L) at position 4; (d) Serine (S) at position 10; (e) Arginine (R) at position 47; (e) Serine (S) at position 57; (f) phenylalanine (F) at position 91; and (g) Valine (V) at position 103.

One can use any of a variety of available methods to produce a humanized antibody comprising a mutation as described above.

Accordingly, the present invention provides an immunobinder humanized according to the method described herein.

In certain preferred embodiments, the target antigen of said immunobinder is VEGF or TNFα.

The polypeptides described in the present invention or generated by a method of the present invention can, for example, be synthesized using techniques known in the art. Alternatively nucleic acid molecules encoding the desired variable regions can be synthesized and the polypeptides produced by recombinant methods.

For example, once the sequence of a humanized variable region has been decided upon, that variable region or a polypeptide comprising it can be made by techniques well known in the art of molecular biology. More specifically, recombinant DNA techniques can be used to produce a wide range of polypeptides by transforming a host cell with a nucleic acid sequence (e.g., a DNA sequence that encodes the desired variable region (e.g., a modified heavy or light chain; the variable domains thereof, or other antigen-binding fragments thereof)).

In one embodiment, one can prepare an expression vector including a promoter that is operably linked to a DNA sequence that encodes at least $V_H$ or $V_L$. If necessary, or desired, one can prepare a second expression vector including a promoter that is operably linked to a DNA sequence that encodes the complementary variable domain (i.e., where the parent expression vector encodes $V_H$, the second expression vector encodes $V_L$ and vice versa). A cell line (e.g., an immortalized mammalian cell line) can then be transformed with one or both of the expression vectors and cultured under conditions that permit expression of the chimeric variable domain or chimeric antibody (see, e.g., International Patent Application No. PCT/GB85/00392 to Neuberger et. al.).

In one embodiment, variable regions comprising donor CDRs and acceptor FR amino acid sequences can be made and then changes introduced into the nucleic acid molecules to effect the CDR amino acid substitution.

Exemplary art recognized methods for making a nucleic acid molecule encoding an amino acid sequence variant of a polypeptide include, but are not limited to, preparation by site-directed (or oligonucleotide-mediated) mutagenesis, PCR mutagenesis, and cassette mutagenesis of an earlier prepared DNA encoding the polypeptide.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the parent DNA is altered by first hybridizing an oligonucleotide encoding the desired mutation to a single strand of such parent DNA. After hybridization, a DNA polymerase is used to synthesize an entire second strand, using the hybridized oligonucleotide as a primer, and using the single strand of the parent DNA as a template. Thus, the oligonucleotide encoding the desired mutation is incorporated in the resulting double-stranded DNA.

PCR mutagenesis is also suitable for making amino acid sequence variants of polypeptides. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the DNA to be mutated. The codon(s) in the parent DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA encoding the polypeptide. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

A variable region generated by the methods of the invention can be re-modeled and further altered to further increase antigen binding. Thus, the steps described above can be preceded or followed by additional steps, including, e.g. affinity maturation. In addition, empirical binding data can be used for further optimization.

It will be understood by one of ordinary skill in the art that the polypeptides of the invention may further be modified such that they vary in amino acid sequence, but not in desired activity. For example, additional nucleotide substitutions leading to amino acid substitutions at "non-essential" amino acid residues may be made to the protein For example, a nonessential amino acid residue in an immunoglobulin polypeptide may be replaced with another amino acid residue from the same side chain family. In another embodiment, a string of amino acids can be replaced with a structurally similar string that differs in order and/or composition of side chain family members, i.e., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Aside from amino acid substitutions, the present invention contemplates other modifications, e.g., to Fc region amino acid sequences in order to generate an Fc region variant with altered effector function. One may, for example, delete one or more amino acid residues of the Fc region in order to reduce or enhance binding to an FcR. In one embodiment, one or more of the Fc region residues can be modified in order to generate such an Fc region variant. Generally, no more than one to about ten Fc region residues will be deleted according to this embodiment of the invention. The Fc region herein comprising one or more amino acid deletions will preferably retain at least about 80%, and preferably at least about 90%, and most preferably at least about 95%, of the starting Fc region or of a native sequence human Fc region.

One may also make amino acid insertion Fc region variants, which variants have altered effector function. For example, one may introduce at least one amino acid residue (e.g. one to two amino acid residues and generally no more than ten residues) adjacent to one or more of the Fc region positions identified herein as impacting FcR binding. By "adjacent" is meant within one to two amino acid residues of an Fc region residue identified herein. Such Fc region variants may display enhanced or diminished FcRn binding.

Such Fc region variants will generally comprise at least one amino acid modification in the Fc region. In one embodiment amino acid modifications may be combined. For example, the variant Fc region may include two, three, four, five, etc substitutions therein, e.g. of the specific Fc region positions identified herein. In another embodiment, a polypeptide may have altered binding to FcRn and to another Fc receptor.

In one embodiment, the polypeptides described in the present invention or generated by a method of the present invention, e.g., humanized Ig variable regions and/or polypeptides comprising humanized Ig variable regions may be produced by recombinant methods. For example, a polynucleotide sequence encoding a polypeptide can be inserted in a suitable expression vector for recombinant expression. Where the polypeptide is an antibody, polynucleotides encoding additional light and heavy chain variable regions, optionally linked to constant regions, may be inserted into the same or different expression vector. An affinity tag sequence (e.g. a His(6) tag) may optionally be attached or included within the polypeptide sequence to facilitate downstream purification. The DNA segments encoding immunoglobulin chains are the operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the polypeptide.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Within the scope of the present invention, *E. coli* and *S. cerevisiae* are preferred host cells.

In addition to microorganisms, mammalian tissue culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, 293 cells, myeloma cell lines, transformed B-cells, and hybridomas. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The subject polypeptide can also be incorporated in transgenes for introduction into the genome of a transgenic animal and subsequent expression, e.g., in the milk of a transgenic animal (see, e.g., Deboer et al. U.S. Pat. No. 5,741,957; Rosen U.S. Pat. No. 5,304,489; and Meade U.S. Pat. No. 5,849,992. Suitable transgenes include coding sequences for light and/or heavy chains in operable linkage with a promoter and enhancer from a mammary gland specific gene, such as casein or beta lactoglobulin.

Polypeptides can be expressed using a single vector or two vectors. For example, antibody heavy and light chains may be cloned on separate expression vectors and co-transfected into cells.

In one embodiment, signal sequences may be used to facilitate expression of polypeptides of the invention.

Once expressed, the polypeptides can be purified according to standard procedures of the art, including ammonium sulfate precipitation, affinity columns (e.g., protein A or protein G), column chromatography, HPLC purification, gel electrophoresis and the like (see generally Scopes, Protein Purification (Springer-Verlag, N.Y., (1982)).

Either the humanized Ig variable regions or polypeptides comprising them can be expressed by host cells or cell lines in culture. They can also be expressed in cells in vivo. The cell line that is transformed (e.g., transfected) to produce the altered antibody can be an immortalized mammalian cell line, such as those of lymphoid origin (e.g., a myeloma, hybridoma, trioma or quadroma cell line). The cell line can also include normal lymphoid cells, such as B-cells, that have been immortalized by transformation with a virus (e.g., the Epstein-Barr virus).

Although typically the cell line used to produce the polypeptide is a mammalian cell line, cell lines from other sources (such as bacteria and yeast) can also be used. In particular, *E. coli*-derived bacterial strains can be used, especially, e.g., phage display.

Some immortalized lymphoid cell lines, such as myeloma cell lines, in their normal state, secrete isolated Ig light or heavy chains. If such a cell line is transformed with a vector that expresses an altered antibody, prepared during the process of the invention, it will not be necessary to carry out the remaining steps of the process, provided that the normally secreted chain is complementary to the variable domain of the Ig chain encoded by the vector prepared earlier.

If the immortalized cell line does not secrete or does not secrete a complementary chain, it will be necessary to introduce into the cells a vector that encodes the appropriate complementary chain or fragment thereof.

In the case where the immortalized cell line secretes a complementary light or heavy chain, the transformed cell line may be produced for example by transforming a suitable bacterial cell with the vector and then fusing the bacterial cell with the immortalized cell line (e.g., by spheroplast fusion). Alternatively, the DNA may be directly introduced into the immortalized cell line by electroporation.

In one embodiment, a humanized Ig variable region as described in the present invention or generated by a method of the present invention can be present in an antigen-binding fragment of any antibody. The fragments can be recombinantly produced and engineered, synthesized, or produced by digesting an antibody with a proteolytic enzyme. For example, the fragment can be a Fab fragment; digestion with papain breaks the antibody at the region, before the interchain (i.e., $V_H$-$V_H$) disulphide bond, that joins the two heavy chains. This results in the formation of two identical fragments that contain the light chain and the $V_H$ and $C_H1$ domains of the heavy chain. Alternatively, the fragment can be an F(ab')$_2$ fragment. These fragments can be created by digesting an antibody with pepsin, which cleaves the heavy chain after the inter-chain disulfide bond, and results in a fragment that contains both antigen-binding sites. Yet another alternative is to use a "single chain" antibody. Single-chain Fv (scFv) fragments can be constructed in a variety of ways. For example, the C-terminus of $V_H$ can be linked to the N-terminus of $V_L$. Typically, a linker (e.g., (GGGGS)$_4$; SEQ ID NO: 8) is placed between $V_H$ and $V_L$. However, the order in which the chains can be linked can be reversed, and tags that facilitate detection or purification (e.g., Myc-, His-, or FLAG-tags) can be included (tags such as these can be appended to any antibody or antibody fragment of the invention; their use is not restricted to scFv). Accordingly, and as noted below, tagged antibodies are within the scope of the present invention. In alternative embodiments, the antibodies described herein, or generated by the methods described herein, can be heavy chain dimers or light chain dimers. Still further, an antibody light or heavy chain, or portions thereof, for example, a single domain antibody (DAb), can be used.

In another embodiment, a humanized Ig variable region as described in the present invention or generated by a method of the present invention is present in a single chain antibody (ScFv) or a minibody (see e.g., U.S. Pat. No. 5,837,821 or WO 94/09817A1). Minibodies are dimeric molecules made up of two polypeptide chains each comprising an ScFv molecule (a single polypeptide comprising one or more antigen binding sites, e.g., a $V_L$ domain linked by a flexible linker to a $V_H$ domain fused to a CH3 domain via a connecting peptide). ScFv molecules can be constructed in a $V_H$-linker-$V_L$ orientation or $V_L$-linker-$V_H$ orientation. The flexible hinge that links the $V_L$ and $V_H$ domains that make up the antigen binding site preferably comprises from about 10 to about 50 amino acid residues. An exemplary connecting peptide for this purpose is (Gly4Ser)3 (SEQ ID NO: 27) (Huston et al. (1988). PNAS, 85:5879). Other connecting peptides are known in the art.

Methods of making single chain antibodies are well known in the art, e.g., Ho et al. (1989), *Gene*, 77:51; Bird et al. (1988), *Science* 242:423; Pantoliano et al. (1991), *Biochemistry* 30:10117; Milenic et al. (1991), *Cancer Research*, 51:6363; Takkinen et al. (1991), *Protein Engineering* 4:837. Minibodies can be made by constructing an ScFv component and connecting peptide-$CH_3$ component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis. In one embodiment, a minibody of the invention comprises a connecting peptide. In one embodiment, the connecting peptide comprises a Gly/Ser linker, e.g., GGGSSGGGSGG (SEQ ID NO: 28).

In another embodiment, a tetravalent minibody can be constructed. Tetravalent minibodies can be constructed in the same manner as minibodies, except that two ScFv molecules are linked using a flexible linker, e.g., having an amino acid sequence $(G_4S)_4G_3AS$ (SEQ ID NO: 29).

In another embodiment, a humanized variable region as described in the present invention or generated by a method of the present invention can be present in a diabody. Diabodies are similar to scFv molecules, but usually have a short (less than 10 and preferably 1-5) amino acid residue linker connecting both variable domains, such that the $V_L$ and $V_H$ domains on the same polypeptide chain can not interact. Instead, the $V_L$ and $V_H$ domain of one polypeptide chain interact with the $V_H$ and $V_L$ domain (respectively) on a second polypeptide chain (WO 02/02781).

In another embodiment, a humanized variable region of the invention can be present in an immunoreactive fragment or portion of an antibody (e.g. an scFv molecule, a minibody, a tetravalent minibody, or a diabody) operably linked to an FcR binding portion. In an exemplary embodiment, the FcR binding portion is a complete Fc region.

Preferably, the humanization methods described herein result in Ig variable regions in which the affinity for antigen is not substantially changed compared to the donor antibody.

In one embodiment, polypeptides comprising the variable domains of the instant invention bind to antigens with a binding affinity greater than (or equal to) an association constant Ka of about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, or $10^{12}$ $M^{-1}$, (including affinities intermediate of these values).

Affinity, avidity, and/or specificity can be measured in a variety of ways. Generally, and regardless of the precise manner in which affinity is defined or measured, the methods of the invention improve antibody affinity when they generate an antibody that is superior in any aspect of its clinical application to the antibody (or antibodies) from which it was made (for example, the methods of the invention are considered effective or successful when a modified antibody can be administered at a lower dose or less frequently or by a more convenient route of administration than an antibody (or antibodies) from which it was made).

More specifically, the affinity between an antibody and an antigen to which it binds can be measured by various assays, including, e.g., an ELISA assay, a BiaCore assay or the KinExA™ 3000 assay (available from Sapidyne Instruments (Boise, Id.)). Briefly, sepharose beads are coated with antigen (the antigen used in the methods of the invention can be any antigen of interest (e.g., a cancer antigen; a cell surface protein or secreted protein; an antigen of a pathogen (e.g., a bacterial or viral antigen (e.g., an HIV antigen, an influenza antigen, or a hepatitis antigen)), or an allergen) by covalent attachment. Dilutions of antibody to be tested are prepared and each dilution is added to the designated wells on a plate. A detection antibody (e.g. goat anti-human IgG-HRP conjugate) is then added to each well followed by a chromagenic substrate (e.g. HRP). The plate is then read in ELISA plate reader at 450 nM, and EC50 values are calculated. (It is understood, however, that the methods described here are generally applicable; they are not limited to the production of antibodies that bind any particular antigen or class of antigens.)

Those of ordinary skill in the art will recognize that determining affinity is not always as simple as looking at a single figure. Since antibodies have two arms, their apparent affinity is usually much higher than the intrinsic affinity between the variable region and the antigen (this is believed to be due to avidity). Intrinsic affinity can be measured using scFv or Fab fragments.

In another aspect, the present invention features bispecific molecules comprising a humanized rabbit antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, tumor specific or pathogen specific antigens, peptide or binding mimetic, such that a bispecific molecule results. Accordingly, the present invention includes bispecific molecules comprising at least one first binding molecule having specificity for a first target and a second binding molecule having specificity for one or more additional target epitope.

In one embodiment, the bispecific molecules of the invention comprise as a binding specificity at least one antibody, or an antibody fragment thereof, including, e.g., an Fab, Fab', $F(ab')_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (MA), flow cytometry based single cell sorting (e.g. FACS analysis), bioassay (e.g., growth inhibition), or Western Blot assay. Each of these assays generally detects the presence of protein-antibody complexes of particular interest by employing a labeled reagent (e.g., an antibody) specific for the complex of interest. For example, the antibody complexes can be detected using e.g., an enzyme-linked antibody or antibody fragment which recognizes and specifically binds to the antibody-VEGF complexes. Alternatively, the complexes can be detected using any of a variety of other immunoassays. For example, the antibody can be radioactively labeled and used in a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

In another aspect, the present invention features a humanized rabbit antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

In one aspect the invention provides pharmaceutical formulations comprising humanized rabbit antibodies for the treatment disease. The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

A "stable" formulation is one in which the antibody or antibody derivative therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year for at least 2 years. Furthermore, the formulation is preferably stable following freezing (to, e.g., −70° C.) and thawing of the formulation.

An antibody or antibody derivative "retains its physical stability" in a pharmaceutical formulation if it shows no signs of aggregation, precipitation and/or denaturation upon visual examination of color and/or clarity, or as measured by UV light scattering or by size exclusion chromatography.

An antibody or antibody derivative "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

An antibody or antibody derivative "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay, for example. Other "biological activity" assays for antibodies are elaborated herein below.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

A "polyol" is a substance with multiple hydroxyl groups, and includes sugars (reducing and non-reducing sugars), sugar alcohols and sugar acids. Preferred polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "non-reducing sugar" is one which does not have these properties of a reducing sugar. Examples of reducing sugars are fructose, mannose, maltose, lactose, arabinose, xylose, ribose, rhamnose, galactose and glucose. Non-reducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is preferably one which does not crystallize at freezing temperatures (e.g. −20° C.) such that it destabilizes the antibody in the formulation. Non-reducing sugars such as sucrose and trehalose are the preferred polyols herein, with trehalose being preferred over sucrose, because of the superior solution stability of trehalose.

As used herein, "buffer" refers to a buffered solution that resists changes in pH by the action of its acid-base conjugate components. The buffer of this invention has a pH in the range from about 4.5 to about 6.0; preferably from about 4.8 to about 5.5; and most preferably has a pH of about 5.0. Examples of buffers that will control the pH in this range include acetate (e.g. sodium acetate), succinate (such as sodium succinate), gluconate, histidine, citrate and other organic acid buffers. Where a freeze-thaw stable formulation is desired, the buffer is preferably not phosphate.

In a pharmacological sense, in the context of the present invention, a "therapeutically effective amount" of an antibody or antibody derivative refers to an amount effective in the prevention or treatment of a disorder for the treatment of which the antibody or antibody derivative is effective. A "disease/disorder" is any condition that would benefit from treatment with the antibody or antibody derivative. This includes chronic and acute disorders or diseases including those pathological conditions which predispose the mammal to the disorder in question.

A "preservative" is a compound which can be included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

The present invention also provides pharmaceutical compositions comprising one or more antibodies or antibody derivative compounds, together with at least one physiologically acceptable carrier or excipient. Pharmaceutical compositions may comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

A carrier is a substance that may be associated with an antibody or antibody derivative prior to administration to a patient, often for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

Pharmaceutical compositions may be formulated for any appropriate manner of administration, including, for example, topical, oral, nasal, rectal or parenteral administration. In certain embodiments, compositions in a form suitable for oral use are preferred. Such forms include, for example, pills, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. The term parenteral as used herein includes subcutaneous, intradermal, intravascular (e.g., intravenous), intramuscular, spinal, intracranial, intrathecal and intraperitoneal injection, as well as any similar injection or infusion technique.

Compositions intended for oral use may be prepared according to any method known to the art for the manufacture of pharmaceutical compositions and may contain one or more agents, such as sweetening agents, flavoring agents, coloring agent, and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil). Aqueous suspensions contain the antibody or antibody derivative in admixture with excipients suitable for the manufacture of aqueous suspensions. Such excipients include suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl or n-propyl p-hydroxybenzoate, one or more coloring agents, one or more flavoring agents, and one or more sweetening agents, such as sucrose or saccharin. Syrups and elixirs may be formulated with sweetening agents, such as glycerol, propylene glycol, sorbitol, or sucrose. Such formulations may also comprise one or more demulcents, preservatives, flavoring agents, and/or coloring agents.

Oily suspensions may be formulated by suspending the active ingredients in a vegetable oil (e.g., arachis oil, olive oil, sesame oil, or coconut oil) or in a mineral oil such as liquid paraffin. The oily suspensions may contain a thickening agent such as beeswax, hard paraffin, or cetyl alcohol. Sweetening agents, such as those set forth above, and/or flavoring agents may be added to provide palatable oral preparations. Such suspensions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin), or a mixture thereof. Suitable emulsifying agents include naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monooleate), and condensation products of partial esters derived from fatty acids and hexitol with ethylene oxide (e.g., polyoxyethylene sorbitan monoleate). An emulsion may also comprise one or more sweetening and/or flavoring agents.

The pharmaceutical composition may be prepared as a sterile injectable aqueous or oleaginous suspension in which the modulator, depending on the vehicle and concentration used, is either suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid may be used in the preparation of injectable compositions, and adjuvants such as local anesthetics, preservatives and/or buffering agents can be dissolved in the vehicle.

Pharmaceutical compositions may be formulated as sustained release formulations (i.e., a formulation such as a capsule that effects a slow release of modulator following administration). Such formulations may generally be prepared using well known technology and administered by, for example, oral, rectal, or subcutaneous implantation, or by implantation at the desired target site. Carriers for use within such formulations are biocompatible, and may also be biodegradable; preferably the formulation provides a relatively constant level of modulator release. The amount of an antibody or antibody derivative contained within a sustained release formulation depends upon, for example, the site of implantation, the rate and expected duration of release and the nature of the disease/disorder to be treated or prevented.

Antibody or antibody derivatives provided herein are generally administered in an amount that achieves a concentration in a body fluid (e.g., blood, plasma, serum, CSF, synovial fluid, lymph, cellular interstitial fluid, tears or urine) that is sufficient to detectably bind to a target such as e.g. VEGF and prevent or inhibit such target mediated diseases/disorders, e.g. VEGF-mediated diseases/disorders. A dose is considered to be effective if it results in a discernible patient benefit as described herein. Preferred systemic doses range from about 0.1 mg to about 140 mg per kilogram of body weight per day (about 0.5 mg to about 7 g per patient per day), with oral doses generally being about 5-20 fold higher than intravenous doses. The amount of antibody or antibody derivative that may be combined with the carrier materials to produce a single dosage form will vary depending upon the host treated and the particular mode of administration. Dosage unit forms will generally contain between from about 1 mg to about 500 mg of an active ingredient.

Pharmaceutical compositions may be packaged for treating conditions responsive to an antibody or antibody derivative directed e.g. to VEGF. Packaged pharmaceutical compositions may include a container holding a effective amount of at least one antibody or antibody derivative as described herein and instructions (e.g., labeling) indicating that the contained composition is to be used for treating a disease/disorder responsive to one antibody or antibody derivative following administration in the patient.

The antibodies or antibody derivatives of the present invention can also be chemically modified. Preferred modifying groups are polymers, for example an optionally substituted straight or branched chain polyalkene, polyalkenylene, or polyoxyalkylene polymer or a branched or unbranched polysaccharide. Such effector group may increase the half-live of the antibody in vivo. Particular examples of synthetic polymers include optionally substituted straight or branched chain poly(ethyleneglycol) (PEG), poly(propyleneglycol), poly(vinylalcohol) or derivatives thereof. Particular naturally occurring polymers include lactose, amylose, dextran, glycogen or derivatives thereof. The size of the polymer may be varied as desired, but will generally be in an average molecular weight range from 500 Da to 50000 Da. For local application where the antibody is designed to penetrate tissue, a preferred molecular weight of the polymer is around 5000 Da. The polymer molecule can be attached to the antibody, in particular to the C-terminal end of the Fab fragment heavy chain via a covalently linked hinge peptide as described in WO0194585. Regarding the attachment of PEG moieties, reference is made to "Poly (ethyleneglycol) Chemistry, Biotechnological and Biomedical Applications", 1992, J. Milton Harris (ed), Plenum Press, New York and "Bioconjugation Protein Coupling Techniques for the Biomedical Sciences", 1998, M. Aslam and A. Dent, Grove Publishers, New York.

After preparation of the antibody or antibody derivative of interest as described above, the pharmaceutical formulation comprising it is prepared. The antibody to be formulated has not been subjected to prior lyophilization and the formulation of interest herein is an aqueous formulation. Preferably the antibody or antibody derivative in the formulation is an antibody fragment, such as an scFv. The therapeutically effective amount of antibody present in the formulation is determined by taking into account the desired dose volumes and mode(s) of administration, for example. From about 0.1 mg/ml to about 50 mg/ml, preferably from about 0.5 mg/ml to about 25 mg/ml and most preferably from about 2 mg/ml to about 10 mg/ml is an exemplary antibody concentration in the formulation.

An aqueous formulation is prepared comprising the antibody or antibody derivative in a pH-buffered solution. The buffer of this invention has a pH in the range from about 4.5 to about 6.0, preferably from about 4.8 to about 5.5, and most preferably has a pH of about 5.0. Examples of buffers that will control the pH within this range include acetate (e.g. sodium acetate), succinate (such as sodium succinate), gluconate, histidine, citrate and other organic acid buffers. The buffer concentration can be from about 1 mM to about 50 mM, preferably from about 5 mM to about 30 mM, depending, for example, on the buffer and the desired isotonicity of the formulation. The preferred buffer is sodium acetate (about 10 mM), pH 5.0.

A polyol, which acts as a tonicifier and may stabilize the antibody, is included in the formulation. In preferred embodiments, the formulation does not contain a tonicifying amount of a salt such as sodium chloride, as this may cause the antibody or antibody derivative to precipitate and/or may result in oxidation at low pH. In preferred embodiments, the polyol is a non-reducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, preferably in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant is also added to the antibody or antibody derivative formulation. Exemplary surfactants include non-ionic surfactants such as polysorbates (e.g. polysorbates 20, 80 etc) or poloxamers (e.g. poloxamer 188). The amount of surfactant added is such that it reduces aggregation of the formulated antibody/antibody derivative and/or minimizes the formation of particulates in the formulation and/or reduces adsorption. For example, the surfactant may be present in the formulation in an amount from about 0.001% to about 0.5%, preferably from about 0.005% to about 0.2% and most preferably from about 0.01% to about 0.1%.

In one embodiment, the formulation contains the above-identified agents (i.e. antibody or antibody derivative, buffer, polyol and surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, most preferably from about 0.5% to about 1%. One or more other pharmaceutically acceptable carriers, excipients or stabilizers such as those described in Remington's Pharmaceutical Sciences 21st edition, Osol, A. Ed. (2006) may be included in the formulation provided that they do not adversely affect the desired characteristics of the formulation. Acceptable carriers, excipients or stabilizers are non-toxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The formulations to be used for in vivo administration must be sterile. This is readily accomplished by filtration through sterile filtration membranes, prior to, or following, preparation of the formulation.

The formulation is administered to a mammal in need of treatment with the antibody, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In preferred embodiments, the formulation is administered to the mammal by intravenous administration. For such purposes, the formulation may be injected using a syringe or via an IV line, for example.

The appropriate dosage ("therapeutically effective amount") of the antibody will depend, for example, on the condition to be treated, the severity and course of the condition, whether the antibody is administered for preventive or therapeutic purposes, previous therapy, the patient's clinical history and response to the antibody, the type of antibody used, and the discretion of the attending physician. The antibody or antibody derivative is suitably administered to the patent at one time or over a series of treatments and may be administered to the patent at any time from diagnosis onwards. The antibody or antibody derivative may be administered as the sole treatment or in conjunction with other drugs or therapies useful in treating the condition in question.

As a general proposition, the therapeutically effective amount of the antibody or antibody derivative administered will be in the range of about 0.1 to about 50 mg/kg of patent body weight whether by one or more administrations, with the typical range of antibody used being about 0.3 to about 20 mg/kg, more preferably about 0.3 to about 15 mg/kg, administered daily, for example. However, other dosage regimens may be useful. The progress of this therapy is easily monitored by conventional techniques.

In another embodiment of the invention, an article of manufacture is provided comprising a container which holds the pharmaceutical formulation of the present invention, preferably an aqueous formulation, and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

In certain preferred embodiments, the article of manufacture comprises a lyophilized immunobinder as described herein or generated by the methods described herein.

EXEMPLIFICATION

The present disclosure is further illustrated by the following examples, which should not be construed as further limiting. The contents of all figures and all references, patents and published patent applications cited throughout this application are expressly incorporated herein by reference in their entireties.

Materials and Methods

In general, the practice of the present invention employs, unless otherwise indicated, conventional techniques of chemistry, molecular biology, recombinant DNA technology, immunology (especially, e.g., antibody technology), and standard techniques of polypeptide preparation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992). Methods of grafting CDRs from rabbit and other non-human monoclonal antibodies onto selected human antibody frameworks is described in detail above. Examples of such grafting experiments are set forth below.

For purposes of better understanding, grafts denominated "min" are those where CDRs were grafted onto framework 1.4 or a variable domain thereof, whereas grafts named "max" are those where CDRs were grafted onto framework 1.4 or a variable domain thereof and wherein the framework further comprises donor framework residues which interact with the antigen.

Example 1: Design of rFW1.4

1.1. Primary Sequence Analysis and Database Searching
1.1.1. Collection of Rabbit Immunoglobulin Sequences Sequences of variable domains of rabbit mature antibodies and germlines were collected from different open source databases (e.g. Kabat database and IMGT) and entered into a customized database as one letter code amino acid sequences. For the entire analysis we used only the amino acid portion corresponding to the V (variable) region. Sequences in the KDB database less than 70% complete or containing multiple undetermined residues in the framework regions were discarded. Sequences with more than 95% identity to any other sequence within the database were also excluded to avoid random noise in the analysis.

1.1.2. Alignments and Numbering of Rabbit Sequences

Rabbit antibody sequences were aligned using conventional sequence alignment tools based on the Needleman-Wunsch algorithm and Blossum matrices. The introduction of gaps and nomenclature of residue positions were done following AHo's numbering system for immunoglobulin variable domains (Honegger and Pluckthun, 2001). The Kabat numbering scheme was also applied in parallel since it is the most widely adopted standard for numbering the residues in an antibody. Kabat numbering was assigned using the SUBIM program. This program analyses variable regions of an antibody sequence and numbers the sequence according to the system established by Kabat and co-workers (Deret et al 1995).

The definition of framework and CDR regions was done following the Kabat definition which is based on sequence variability and is the most commonly used. Nevertheless, CDR-H1 designation was a compromise between different definitions including, AbM's, kabat's, mean contact data generated by analysis of contacts between antibody and antigen of a subset of 3D complex structures (MacCallum et al., 1996) and Chotia's which is based on the location of the structural loop regions (described above and shown in FIG. 1).

1.1.3. Frequency and Conservation of Residue Positions

Amino acid sequence diversity was analyzed using a set of 423 rabbit sequences from the kabat database. The residue frequency, f(r), for each position, i, in the mature rabbit sequences was calculated by the number of times that particular residue is observed within the data set divided by the total number of sequences. The degree of conservation for each position, i, was calculated using the Simpson's index, which takes into account the number of different amino acids present, as well as the relative abundance of each residue.

$$D = \frac{\sum_{i=1}^{r} n(n-1)}{N(N-1)}$$

where: N Total number of amino acids, r is the number of different amino acids present at each position and n is the number of residues of a particular amino acid type.

1.1.4. Lineage Analysis of the Rabbit V Region

Phylogeny analysis tools were used to study the rabbit repertoire. Amino acids sequences of the V region were clustered using both cluster and topological algorithms. The distance matrix was calculated for the whole array and used as indication of the germline usage. Consensus sequence of each cluster was calculated and the nearest rabbit germline sequence counterpart identified. Also the overall consensus sequence was derived for the whole set of sequences.

1.1.5. Assignment of Human Subgroup.

For each rabbit representative sequence of the different clusters, the most homologous human sub-group was identified using an EXCEL implementation of sequence analysis algorithms and classification methods based on analysis of the human antibody repertoire (Knappik et al., 2000).

1.2. Design of the Human Acceptor Framework

With the blueprint of the rabbit repertoire from the sequence analysis described above, residues in the framework generally involved in the positioning of rabbit CDRs were identified. Among the frameworks having high homology relative to the rabbit repertoire and the respective clusters, one having good biophysical properties was selected from a pool of fully human sequences. The selected framework to serve as acceptor framework belongs to variable light chain subgroup kappa 1 and heavy variable chain subgroup III with the ESBATech's ID KI 27, a43 correspondingly. This stable and soluble antibody framework has been identified by screening of a human spleen scFv library using a yeast-based screening method named "Quality Control" system (Auf der Maur et al., 2004) and was designated "FW1.4". Although the stable and soluble framework sequence FW1.4 exhibits high homology, it was not the most homologous sequence available. The identified residues were incorporated in said acceptor framework to generate rFW1.4.

With the information for amino acid sequence diversity, germline usage and the structural features of the rabbit antibodies, we analyzed the FW1.4 for compatibility of residue positions required to preserve the CDR conformation in the new human framework. We examined the variable regions of FW1.4 for compatibility of the following characteristics:

i. Residues that are part of the canonical sequences for loop structures.
ii. Framework residues located at the VL/VH interface.
iii. The platform of residues directly underneath the CDRs
iv. Upper and lower core residues
v. Framework residues defining the subtype 1.3. Grafting of Rabbit CDRs Grafts were generated by simply combining the CDR sequences (according above definition) from one antibody with the framework sequence of FW1.4 or the rFW1.4. Residues potentially involved in binding were identified. For each rabbit variable domain sequence, the nearest rabbit germline counterpart was identified. If the closest germline could not be established, the sequence was compared against the subgroup consensus or the consensus of rabbit sequences with a high percentage of similarity. Rare framework residues were considered as possible result of somatic hypermutation and therefore playing a role in binding. Consequently, such residues were grafted onto the acceptor framework.

1.4 Results

By analyzing the rabbit antibody repertoire in terms of structure, amino acid sequence diversity and germline usage, 5 residue positions in the light chain of FW1.4 were found which were modified to maintain loop conformation of rabbit CDRs. These positions are highly conserved in rabbit antibodies. The consensus residue for these 5 positions was deduced from the rabbit repertoire and introduced into the human acceptor framework 1.4. With the modification of these conserved positions, said framework became virtually compatible with all six complementarity determining regions (CDRs) of any rabbit CDRs. The master rFW1.4 containing different rabbit CDRs is well expressed and good produced contrary to the wild type single chains. 16 members derived from the combination of this framework and rabbit CDRs were created detailed characterization showed functionality.

Example 2: B Cell Screening System

Figure 3A:
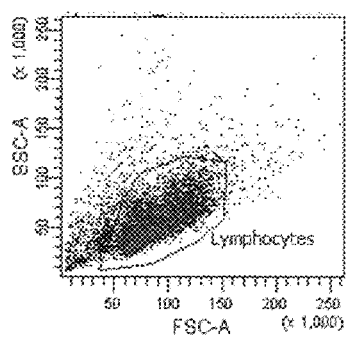
FIGS. 3A, 3B, and 3C: the FACS selection process of rabbit B cells binding to ESBA903 soluble target.
Figure 3B:
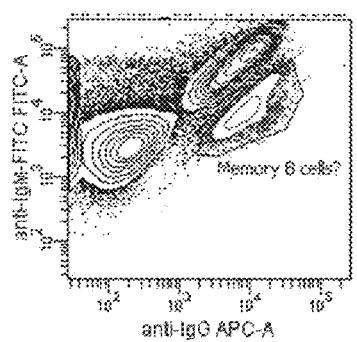
Figure 3C:
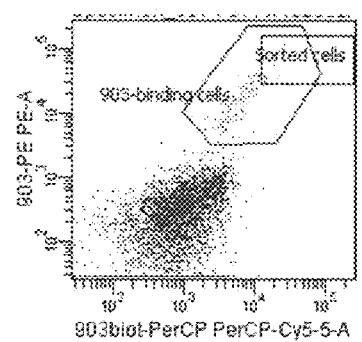

A FACS (flow cytometry based single cell sorting)-based screening system has been established at ESBATech in order to select B cells that bind to a target of interest via their B cell receptors (BCR). One target was for example a soluble protein, namely a single-chain antibody (ESBA903) labeled with a fluorescent dye (PE and PerCP). Lymphocyte suspension was prepared from the spleen of rabbits immunized with the recombinant target. Cells were then incubated with PE and PerCP labeled ESBA903 as well as with antibodies specific for IgG (APC-labeled) or IgM (FITC labeled). ESBA903 positive B-cells that express IgG but not IgM on their surface were sorted in 96-well plates (FIG. 3; table 2). By means of a thymoma helper cell line (EL4-B5: see Zubler et al, 1985, J. Immunol, 134(6): 3662-3668), selected B cells proliferated, differentiated into plasma cells and secreted antibodies. The affinity of these IgGs for the target was verified by ELISA and Biacore measurements. Kinetic parameters are depicted in table 1 for seven selected clones. These clones, from a pool of ~200 sorted cells, show binding affinities in the low nanomolar to picomolar range. Finally, mRNA was isolated from 6 clones of interest and CDRs were grafted on the single-chain framework FW1.4.

TABLE 1

Kinetic values for 7 B cell culture supernatants.

| B-cell clone | ka [Ms$^{-1}$] | kd [s$^{-1}$] | K$_D$ [M] |
|---|---|---|---|
| SG2 | 2.91E+06 | 2.95E−04 | 1.01E−10 |
| SE11 | 3.63E+05 | 3.81E−04 | 1.05E−09 |
| 2E-03 | 8.34E+05 | 3.53E−04 | 4.23E−10 |
| 9E-03 | 8.66E+05 | 6.47E−04 | 7.47E−10 |
| 7D-03 | 3.97E+05 | 3.04E−04 | 7.65E−10 |
| 12B-02 | 1.08E+06 | 1.10E−04 | 1.01E−10 |

TABLE 2

Sorting statistics.

| Population | #events | % parent | % total |
|---|---|---|---|
| All events | 100.000 | #### | 100.0 |
| Lymphocytes | 86.585 | 86.6 | 86.6 |
| Single Lymphocytes 1 | 86.013 | 99.3 | 86.0 |
| Single Lymphocytes 2 | 85.523 | 99.4 | 85.5 |
| Memory B cells? | 5.450 | 6.4 | 5.4 |
| Sorted cells | 16 | 0.3 | 0.0 |
| 903-binding cells | 160 | 2.9 | 0.2 |

Example 3: Detection of the Interaction Between Beads Coated with Anti-TNFalpha Antibody and CHO Cells Expressing Membrane-Bound TNFalpha In order to evaluate whether or not the high pressure in flow-cytometry stream breaks non covalent binding between two cells, the following experiment was performed.

Figure 4:
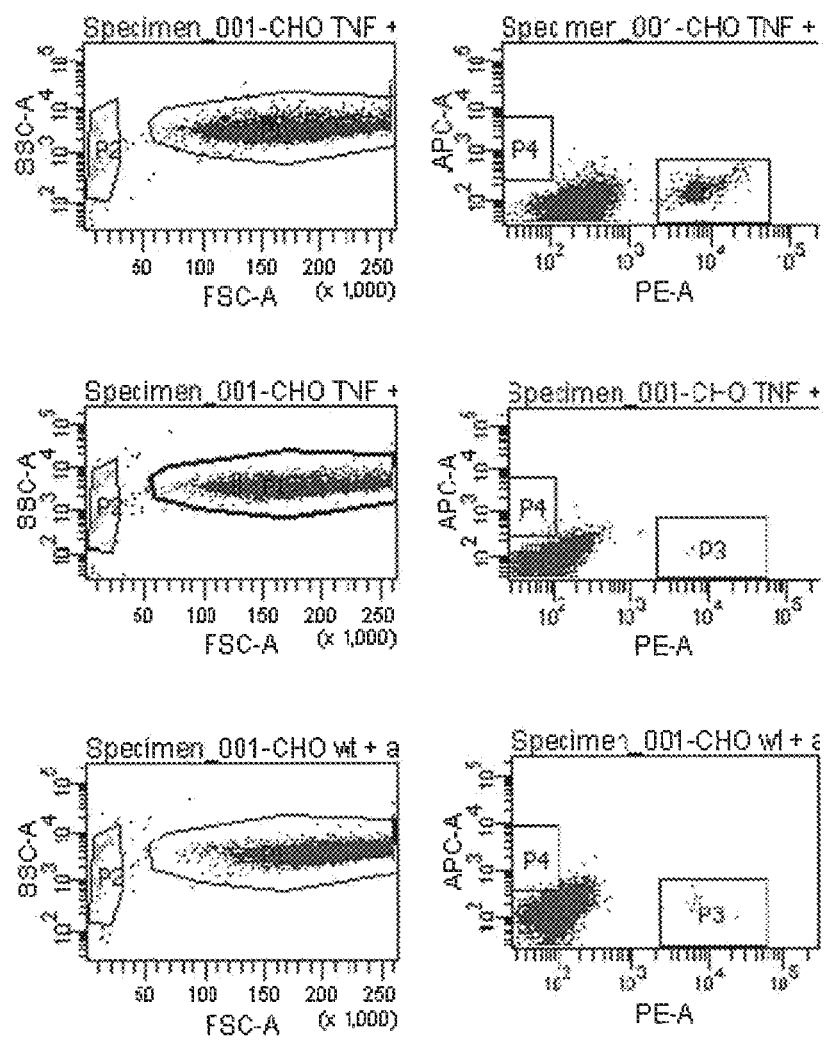
FIG. 4. Beads coated with anti-TNFalpha antibodies (PE labeled) bind to TNFalpha-transfected CHO cells (upper panel). Control beads coated anti-CD19 antibodies (APC labeled) do not bind TNFalpha transfected CHO cells (middle panel). Beads coated with anti-TNFalpha antibodies (PE labeled) do not bind to wildtype (wt) CHO cells (lower panel). Dot plots on the left show forward and side scatters, which indicate respectively the size and the granularity of the events. Single beads (~3 um) population is gated in P2. CHO cells eventually bound to beads (~30 um) are gated in P1. Dot plots in the middle show the P1 events (CHO cells) in respect to their PE or APC staining. Thus, if cells interact with anti-TNFalpha beads, they will be shown in P3 gate, and if they interact with the anti-CD19 beads they will appear in P4 gate. On the right, statistics for each sample are detailed.
Figure 5:
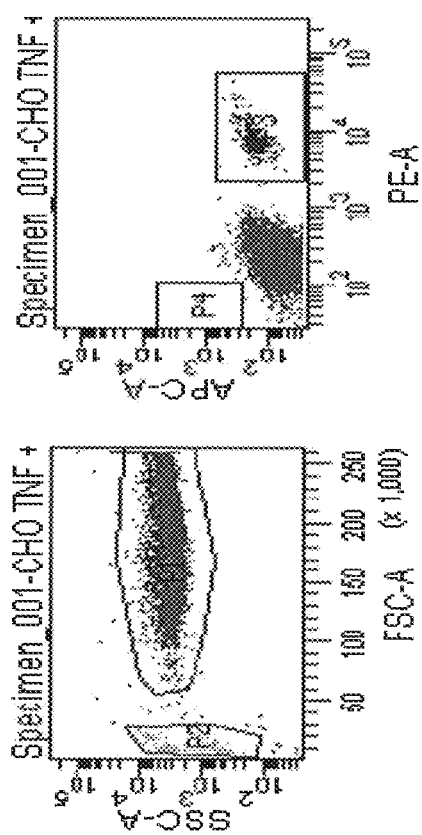
FIG. 5. Beads coated with anti-TNFalpha-PE and beads coated with anti-CD19-APC were mixed together with TNFalpha-transfected CHO cells. CHO cells were gated (P1) and among them cells binding to either anti-TNFalphaPE coated beads or anti-CD19-APC coated beads are shown in gates P3 and P4, respectively. Unbound beads are visible in gate P2.
Figure 6:
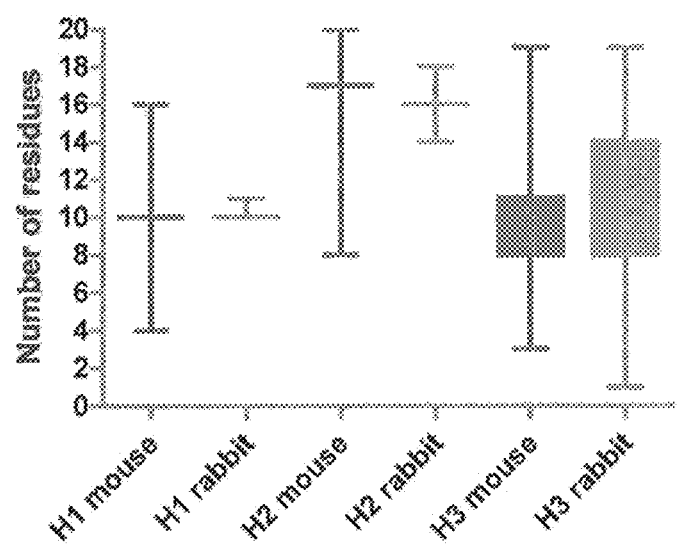
FIG. 6. An analysis of rabbit antibody sequences extracted from the Kabat database confirms that CDR3 of the variable heavy chain is typically by three amino acids longer than its murine counterpart.

CHO cells stably transfected with membrane-bound TNFalpha (B-220 cells) were incubated with beads coated with a PE-labeled anti-TNFalpha antibody. In this set-up the beads mimic memory B cells (they have more or less the same size). As negative controls, non-transfected CHO cells were used, as well as beads coated with an APC labeled unrelated antibody (anti-CD19). After 2 hours incubation at 4° C. with agitation, the cell-bead suspension was analyzed by FACS (using a 130 um nozzle). FIG. 4 shows that a specific binding between anti-TNFalpha □ beads and TNFalpha-transfected CHO cells is clearly detectable with FACS. Indeed, in this sample (upper panel) about two thirds of the beads are bound to cells (585 bound against 267 unbound). In contrast, in the control samples (middle and lower panels), almost no bead binds to CHO cells. Further, both bead populations (anti-TNFalpha-PE and anti-CD19-APC) were mixed together with TNFalpha-transfected CHO cells. FIG. 5 and table 4 shows that about half of the anti-TNFalpha beads bind to CHO cells, whereas the vast majority of the anti-CD19 beads stay unbound. The percentage of beads binding to the cell in each sample is detailed in table 5. Thus, the demonstration is made that the specific selection of single B cells that bind to an integral membrane target protein through their B cell receptor is possible using flow-cytometry.

TABLE 3a

Sorting statistics (see also FIG. 4a)

| Population | # Events | % Parent | % Total |
|---|---|---|---|
| All events | 10.000 | ### | 100.0 |
| P1 | 9.692 | 96.9 | 96.9 |
| P3 | 585 | 6.0 | 5.9 |
| P4 | 1 | 0.0 | 0.0 |
| P2 | 267 | 2.7 | 2.7 |

TABLE 3b

Sorting statistics (see also FIG. 4b)

| Population | # Events | % Parent | % Total |
|---|---|---|---|
| All events | 10.000 | ### | 100.0 |
| P1 | 9.399 | 94.0 | 94.0 |
| P3 | 3 | 0.0 | 0.0 |
| P4 | 6 | 0.1 | 0.1 |
| P2 | 550 | 5.6 | 5.6 |

TABLE 3c

Sorting statistics (see also FIG. 4c)

| Population | # Events | % Parent | % Total |
|---|---|---|---|
| All events | 10.000 | ### | 100.0 |
| P1 | 9.001 | 90.0 | 90.0 |
| P3 | 13 | 0.1 | 0.1 |
| P4 | 7 | 0.1 | 0.1 |
| P2 | 811 | 8.1 | 8.1 |

TABLE 4

Sorting statistics (see also FIG. 5)

| Population | # Events | % Parent | % Total |
|---|---|---|---|
| All events | 10.000 | ### | 100.0 |
| P1 | 9.096 | 91.0 | 91.0 |
| P3 | 401 | 4.4 | 4.0 |
| P4 | 2 | 0.0 | 0.0 |
| P2 | 856 | 8.6 | 8.6 |

TABLE 5

Percentage of beads bound to CHO cells in each sample

| | Cells | mAb on beads | % bound beads |
|---|---|---|---|
| Sample 1 | CHO-TNFα (B220) | anti-TNFα | 68.0 |
| Sample 2 | CHO-TNFα (B220) | anti-CD19 | 0.9 |
| Sample 3 | CHO wt | anti-TNFα | 1.5 |
| Sample 4 | CHO-TNFα (B220) | anti-TNFα | 47.0 |
| | | anti-CD19 | 0.4 |

Example 4: CDR Grafting and Functional Humanization of Anti-TNFα Rabbit Donor Antibodies Four anti-TNFα rabbit antibodies "Rabmabs" (EPI-1, EPI-15, EP-34, EP-35 and EP-42) were selected for CDR grafting. The general experimental scheme for the CDR grafting, humanization, and preliminary characterization of humanized rabbit donor antibodies was done as outlined in the description. Unlike traditional humanization methods which employ the human antibody acceptor framework that shares the greatest sequence homology with the non-human donor antibody, the rabbit CDRs were grafted into a human framework (FW 1.4) that was preselected for desirable functional properties (solubility and stability) using a Quality Control assay (WO0148017). These stable and soluble framework sequence exhibited high homology with the RabMabs.

CDR grafts were generated for each of the RabMabs using the methodology described herein. In "Min" grafts, only the rabbit CDRs were transplanted from the VL and VH domains of the rabbit donor antibody to the human acceptor framework FW1.4. "Max" grafts refer to the grafting of the rabbit CDRs to rFW1.4.

The scFvs described and characterized herein were produced as follows. The humanized VL sequences were connected to humanized VH sequences via the linker of SEQ ID NO:8 to yield an scFv of the following orientation: $NH_2$-VL-linker-VH-COOH. In many cases DNA sequences encoding for the various scFvs were de novo synthesized at the service provider Entelechon GmbH. The resulting DNA inserts were cloned into the bacterial expression vector pGMP002 via NcoI and HindIII restriction sites introduced at the 5' and 3' end of the scFv DNA sequence, respectively. Between the DNA sequence of the VL domain and the VH domain, a BamHI restriction site is located. In some cases the scFv encoding DNA was not de novo synthesized, but the scFv expressing constructs were cloned by domain shuffling. Accordingly, the VL domains were excised and introduced into the new constructs via NcoI and BamHI restriction sites, the VH domains via BamHI and HindIII restriction sites. In other cases, point mutations were introduced into the VH and/or VL domain using state of the art assembling PCR methods. The cloning of GMP002 is described in Example 1 of WO2008006235. The production of the scFvs was done analogue as for ESBA105 as described in Example 1 of WO2008006235.

Table 3 depicts a summary of the detailed characterization data for the four rabbit monoclonals (EP6, EP19, EP34, EP35 and EP43) and their CDR grafted variants. Although the CDR grafts exhibited a broad range of activities in BIACore binding assays and L929, TNFα-mediated cytotoxicity assays, 3 of the 4 maximal ("max") grafts exhibited therapeutically relevant activities. EP43max exhibited the most favorable binding affinity (Kd of 0.25 nM) and an excellent EC50 in the cytotoxicity assay. This data show that FW1.4 (SEQ ID No: 1 and 2) is an exemplary soluble and stable human acceptor framework region for grafting rabbit CDRs.

Potency Assay

The neutralizing activity of anti-TNFα binders was assessed in a L929 TNFα-mediated cytotoxicity assay. Toxicity of Mouse L929 fibroblast cells treated with Actinomycin was induced with recombinant human TNF (hTNF). 90% of maximal hTNF-induced cytotoxicity was determined to be at a TNF concentration of 1000 pg/ml. All L929 cells were cultured in RPMI 1640 with phenolred, with L-Glutamine medium supplemented with fetal calf serum (10% v/v). The neutralizing activity of anti-TNFα binders was assessed in RPMI 1640 without phenolred and 5% fetal calf serum. Different concentrations (0-374 ng/mL) of anti-TNF binders are added to L929 cells in presence of 1000 pg/ml hTNF in order to determine the concentration at which the antagonistic effect reaches half-maximal inhibition (EC50%) The dose response curve was fitted with nonlinear sigmoidal regression with variable slope and the EC50 was calculated.

Biacore Binding Analysis of Anti-TNF scFvs

For binding affinity measurements, surface Plasmon resonance measurements with BIAcore™-T100 were employed using a NTA sensor chip and His-tagged TNF (produced at ESBATech). The surface of the NTA sensor chip consists of a carboxymethylated dextran matrix pre-immobilized with nitrilotriacetic acid (NTA) for capture of histidine tagged molecules via $Ni^{2+}$NTA chelation. Human TNFa N-his trimers (5 nM) are captured by the nickel via their N-terminal his-tags and ESBA105 (analyte) is injected at several concentrations ranging from 30 nM to 0.014 nM in 3 fold serial dilution steps. At the regeneration step, the complex formed by nickel, ligand and analyte is washed away. This allows the use of the same regeneration conditions for different samples. The response signal is generated by surface Plasmon resonance (SPR) technology and measured in resonance units (RU). All the measurements are performed at 25° C. Sensorgrams were generated for each anti-TNF scFv sample after in-line reference cell correction followed by buffer sample subtraction. The apparent dissociation rate constant ($k_d$), the apparent association rate constant ($k_a$) and the apparent dissociation equilibrium constant ($K_D$) were calculated using one-to-one Langmuir binding model with BIAcore T100 evaluation Software version 1.1.

TABLE 3

TNFalpha second generation of binders

| Description | ID | L929* | kon | koff | $K_D$ | FT-IR TM ° C. | RF yield** |
|---|---|---|---|---|---|---|---|
| EP1_min | 1071 | ND*** | — | — | — | — | 2 |
| EP6_min | 673 | ND*** | 4.67E+04 | 4.94E−03 | 1.06E−07 | 50.2 | 35 |
| EP15_min | 1073 | ND*** | 1.57E+05 | 4.10E−02 | 2.62E−07 | — | 41.5 |
| EP19_min | 616 | ND*** | — | — | — | — | — |
| EP34_min | 643 | ND*** | — | — | — | — | — |
| EP35_min | 1075 | ND*** | — | — | — | — | 1 |
| EP42_min | 1076 | ND*** | 1.42E+05 | 8.35E−03 | 5.87E−08 | — | 3 |
| EP43_min | 705 | ND*** | 5.38E+03 | 2.98E−02 | 5.54E−06 | 70.2 | 30.0 |
| EP1_max | 1072 | ND*** | 1.11E+04 | 6.30E−04 | 5.69E−08 | — | 44 |
| EP6_max | 674 | 1.1 | 2.84E+05 | 1.45E−04 | 5.12E−10 | 48.1 | 12 |
| EP15_max | 1074 | 0.39 | 1.53E+06 | 2.26E−03 | 1.48E−09 | 68.6 | 57.8 |
| EP19_max | 1007 | 0.6 | 2.25E+04 | 6.54E−05 | 2.91E−09 | 53.5 | 52 |
| EP34_max | 791 | 10.5 | 5.86E+05 | 1.68E−05 | 2.86E−11 | 72.4 | 4.05 |
| EP35_max | 1089 | 5.20 | 7.72E+05 | 1.50E−04 | 1.94E−10 | — | 0.66 |
| EP42_max | 1077 | ND*** | 1.21E+05 | 4.19E−04 | 3.46E−09 | — | 47.6 |

TABLE 3-continued

TNFalpha second generation of binders

| Description | ID | L929* | kon | koff | $K_D$ | FT-IR TM ° C. | RF yield** |
|---|---|---|---|---|---|---|---|
| EP43_max | 676 | 6.4 | 1.78E+05 | 4.48E−05 | 2.51E−10 | 74.3 | 21.73 |
| EP34min_C-His | 790 | 0.2 | | | | | |
| EP19max_C-His | 789 | 1.9 | | | | | |

*L929 [EC50-E105/EC50-X], compared in mass units [ng/ml] relative to the performance of ESBA105(WO06/131013)
**(mg/L refolding solution);
***Not Determined Example 5: CDR Grafting and Functional Humanization of Anti-VEGF Rabbit Donor Antibodies Eight anti-VEGF Rabmabs (375, 435, 509, 511, 534, 567, 578 and 610) were selected for CDR grafting. Unlike traditional humanization methods which employ the human antibody acceptor framework that shares the greatest sequence homology with the non-human donor antibody, the rabbit CDRs were grafted into a human acceptor framework FW1.4 (SEQ ID No: 1 and 2) that was preselected for desirable functional properties (solubility and stability) using a Quality Control assay (WO0148017).

A number of CDR grafts were generated for each of the RabMabs (rabbit antibodies) using the methodology described herein (see Example 4). "Min" grafts comprised a minimal graft wherein only the rabbit CDRs were transplanted from the VL and VH domains of the rabbit donor antibody to the human acceptor framework FW1.4 (SEQ ID No: 1). "Max" grafts comprised not only the rabbit CDRs for the VL and VH, but also some additional framework residues from the rabbit donor that were predicted to be important for antigen binding. In the case of 578max, the heavy chain variable domain framework region of FW1.4 has additional amino acid alterations at Kabat positions 23H, 49H, 73H, 78H, and 94H.

Table 4 shows a summary of the detailed characterization data for the "Min" and "Max" CDR grafted variants. Their potency as VEGF inhibitors, which is measured using VEGFR competition ELISA and/or HUVEC assay are described. This data shows that FW1.4 (SEQ ID No: 1 and 2) is an exemplary soluble and stable human acceptor framework region for grafting rabbit CDRs.

Biacore Binding Analysis of Anti-VEGF scFvs

The Biacore-binding ability of scFvs was tested and the binding affinity was measured using the exemplary surface plasmon resonance method with BIAcore™-T100. The VEGF proteins, tested for binding by these scFv candidates, in this example and later examples include purified *Escherichia coli*-expressed recombinant human VEGF$_{165}$ (PeproTech EC Ltd.), recombinant human VEGF$_{121}$ (PeproTech EC Ltd.), recombinant human VEGF$_{110}$ (ESBATech AG), recombinant murine VEGF$_{164}$ (PeproTech EC Ltd.), recombinant rat VEGF$_{164}$ (Biovision), recombinant rabbit VEGF$_{110}$ (ESBATech AG), and recombinant human PLGF (PeproTech EC Ltd.). For the surface plasmon resonance experiment, carboxymethylated dextran biosensor chips (CM4, GE Healthcare) were activated with N-ethyl-N'-(3-dimethylaminopropyl) carbodiimide hydrochloride and N-hydroxysuccinimide according to the supplier's instructions. Each of the 6 different VEGF forms, as exemplified above, was coupled to 1 of the 4 different flow cells on a CM4 sensor chip using a standard amine-coupling procedure. The range of responses obtained with these immobilized VEGF molecules after coupling and blocking were ~250-500 response units (RU) for hVEGF$_{165}$, ~200 RU for hVEGF$_{110}$, hVEGF$_{121}$, murine VEGF$_{164}$, rat VEGF$_{164}$ and rabbit VEGF$_{110}$ and ~400 RU for PLGF. The 4th flow cell of each chip was treated similarly except no proteins were immobilized prior to blocking, and the flow cell was used as in-line reference. Various concentrations of anti-VEGF scFvs (e.g., 90 nM, 30 nM, 10 nM, 3.33 nM, 1.11 nM, 0.37 nM, 0.12 nM and 0.04 nM) in HBS-EP buffer (0.01 M HEPES, pH 7.4, 0.15 M NaCl, 3 mM EDTA, 0.005% surfactant P20) were injected into the flow cells at a flow rate of 30 µl/min for 5 min. Dissociation of the anti-VEGF scFv from the VEGF on the CM4 chip was allowed to proceed for 10 min at 25° C. Sensorgrams were generated for each anti-VEGF scFv sample after in-line reference cell correction followed by buffer sample subtraction. The apparent dissociation rate constant ($k_d$), the apparent association rate constant ($k_a$) and the apparent dissociation equilibrium constant ($K_D$) were calculated using one-to-one Langmuir binding model with BIAcore T100 evaluation Software version 1.1.

HUVEC Assay of VEGF Inhibition

The HUVEC assay is a method to measure the potency of the disclosed anti-VEGF scFv candidates as VEGF inhibitors.

Human umbilical vein endothelial cells (HUVECs) (Promocell), pooled from several donors, were used at passage 2 to passage 14. Cells were seeded at 1000 cells/well in 50 µl complete endothelial cell growth medium (ECGM) (Promocell), that contained 0.4% ECGS/H, 2% Fetal Calf Serum, 0.1 ng/ml Epidermal Growth Factor, 1 µg/ml Hydrocortison, 1 ng/ml basic Fibroblast Factor and 1% penicillin/streptomycin (Gibco). 7 to 8 h later, 50 µl starving medium (ECGM without supplements containing 0.5% heat inactivated FCS and 1% penicillin/streptomycin) was added to the cells and the cells were starved for 15 to 16 hours. 3 fold Serial dilutions of anti-VEGF scFvs (0.023-150 nM) and one of the following—recombinant human VEGF$_{165}$ (0.08 nM), recombinant mouse VEGF$_{164}$ (0.08 nM), or recombinant rat VEGF$_{164}$ (0.3 nM)—were prepared in starving medium and preincubated for 30-60 min at room temperature. The different concentrations of VEGFs were used to compensate for their different relative biological activities. Concentrations that stimulate submaximal VEGF induced proliferation (EC$_{90}$) were used. 100 µl of the mixtures were added to the 96-well tissue-culture plates containing the HUVEC suspension and incubated for 4 days in a 37° C./5% CO$_2$ humified incubator. Proliferation of HUVECs was assessed by measuring absorbance at 450 nm (620 nm used as reference wavelength) after addition of 20 µl/well WST-1 cell proliferation reagent (Roche) using a Sunrise microplate reader (Tecan). Data were analyzed using a 4-parameter logistic curve-fit, and the concentration of anti-VEGF scFvs required to inhibit HUVEC proliferation by 50% (EC$_{50}$) was derived from inhibition curves.

TABLE 4

| ID | Protein Nr. | Rel. activity hVEGR2 comp. ELISA ($EC50_{Luc}$ [nM]/$EC50_{test}$ [nM]) | Rel. activity hVEGR1 comp. ELISA ($EC50_{Luc}$ [nM]/$EC50_{test}$ [nM]) | Biacore Measurements hVEGF$_{165}$ ka (1/Ms) | kd (1/s) | KD (M) |
|---|---|---|---|---|---|---|
| 375-min | 857 | 0.3 | ND | 9.27E+05 | 5.01E−03 | 5.41E−09 |
| 375-max | 873 | 0.6 | ND | 2.44E+06 | 6.55E−03 | 2.68E−09 |
| 375-max C-His | 877 | 0.4 | ND | 2.93E+05 | 8.75E−04 | 2.98E−09 |
| 509-min | 854 | 1.0 | 2.9 | 6.23E+05 | 1.14E−03 | 1.82E−09 |
| 509-max | 855 | 4.1 | 13 | 2.26E+06 | 2.72E−03 | 1.21E−09 |
| 509-maxII | 856 | 0.6 | 0.09 | 8.38E+05 | 2.82E−03 | 3.37E−09 |
| 511-min | 801 | 4.9 | 0.7 | 5.05E+05 | 1.28E−03 | 2.53E−09 |
| 511-max | 802 | 8.7 | 8 | 6.59E+05 | 4.40E−05 | 6.67E−11 |
| 534-min C-His | 807 | 0.1 | ND | 2.71E+05 | 9.21E−03 | 3.41E−08 |
| 534-max | 793 | 1.1 | ND | 1.88E+06 | 1.73E−02 | 9.21E−09 |
| 567-min | 884 | 9.7 | 57 | 2.01E+06 | 4.61E−04 | 2.30E−10 |
| 567-max | 874 | 4.1 | 15.7/54.5 | 1.20E+06 | 2.26E−04 | 1.88E−10 |
| 578-min | 820 | 4.1 | 4.8 | 1.14E+06 | 1.03E−02 | 9.01E−09 |
| 578-max | 821 | 9.6 | 35.5/51.6 | 7.00E+05 | 3.07E−04 | 4.39E−10 |
| 610-min | 882 | 0.1 | ND | 2.51E+05 | 2.65E−03 | 1.06E−08 |
| 610-max | 883 | 0.4 | ND | 5.09E+05 | 6.01E−04 | 1.18E−09 |
| 435-min | 944 | ND | ND | ND | ND | ND |
| 435-max | 945 | 7.6 | ND | 1.67E+05 | 7.55E−04 | 4.53E−09 |

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The invention claimed is:

1. A method of humanizing a rabbit immunobinder, the rabbit immunobinder comprising heavy chain CDR H1, CDR H2 and CDR H3 sequences and light chain CDR L1, CDR L2 and CDR L3 sequences, the method comprising:
   (i) grafting the rabbit CDR H1, CDR H2 and CDR H3 sequences into a human heavy chain acceptor framework that is at least 85% identical to the sequence of SEQ ID NO: 4 and that comprises a threonine (T) at position 24 (AHo numbering), alanine (A) or glycine (G) at position 56, threonine (T) or asparagine (N) at position 84, and leucine (L) or valine (V) at position 89 (AHo numbering), and
   (ii) grafting the rabbit CDR L1, CDR L2 and CDR L3 sequences into a human light chain acceptor framework, the human light chain framework having at least 85% identity to SEQ ID NO:2.

2. The method of claim 1, wherein the amino acid sequence of the heavy chain acceptor framework comprises alanine (A) or glycine (G) at position 56, threonine (T) at position 84, valine (V) at position 89, and arginine (R) at position 108 (AHo numbering).

* * * * *

SEQUENCE LISTING

```
<160> NUMBER OF SEQ ID NOS: 29

<210> SEQ ID NO 1
<211> LENGTH: 232
<212> TYPE: PRT
<213> ORGANISM: Artificial Sequence
<220> FEATURE:
<223> OTHER INFORMATION: variable heavy chain framework of FW1.4 (a43)
<220> FEATURE:
<221> NAME/KEY: MISC_FEATURE
<222> LOCATION: (26)..(75)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: Xaa can be any naturally occurring amino acid.
      at least three and up to 50 amino acids can be present

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45
```

```
Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Val Arg Gln Ala
65                  70                  75                  80

Pro Gly Lys Gly Leu Glu Trp Val Ser Xaa Xaa Xaa Xaa Xaa
                85                  90                  95

Xaa Xaa Xaa Xaa Xaa Xaa Xaa Xaa Xaa Xaa Xaa Xaa Xaa Xaa
               100                 105                 110

Xaa Xaa Xaa Xaa Xaa Xaa Xaa Xaa Xaa Xaa Xaa Xaa Xaa Xaa
               115                 120                 125

Xaa Xaa Xaa Xaa Xaa Xaa Xaa Xaa Xaa Arg Phe Thr Ile Ser
           130                 135                 140

Arg Asp Asn Ser Lys Asn Thr Leu Tyr Leu Gln Met Asn Ser Leu Arg
145                 150                 155                 160

Ala Glu Asp Thr Ala Val Tyr Tyr Cys Ala Lys Xaa Xaa Xaa Xaa Xaa
                165                 170                 175

Xaa Xaa Xaa Xaa Xaa Xaa Xaa Xaa Xaa Xaa Xaa Xaa Xaa Xaa
               180                 185                 190

Xaa Xaa Xaa Xaa Xaa Xaa Xaa Xaa Xaa Xaa Xaa Xaa Xaa Xaa
           195                 200                 205

Xaa Xaa Xaa Xaa Xaa Xaa Xaa Xaa Xaa Xaa Xaa Xaa Trp Gly Gln
       210                 215                 220

Gly Thr Leu Val Thr Val Ser Ser
225                 230

<210> SEQ ID NO 2
<211> LENGTH: 231
<212> TYPE: PRT
<213> ORGANISM: Artificial Sequence
<220> FEATURE:
<223> OTHER INFORMATION: variable light chain framework of FW1.4(KI27)
<220> FEATURE:
<221> NAME/KEY: MISC_FEATURE
<222> LOCATION: (24)..(73)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: Xaa can be any naturally occurring amino acid.
      at least three and up to 50 amino acids can be present

<400> SEQUENCE: 2

Glu Ile Val Met Thr Gln Ser Pro Ser Thr Leu Ser Ala Ser Val Gly
1               5                  10                  15

Asp Arg Val Ile Ile Thr Cys Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95
```

```
Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Gly Val Pro Ser Arg Phe
        130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Phe Gly Gln Gly
        210                 215                 220

Thr Lys Leu Thr Val Leu Gly
225                 230

<210> SEQ ID NO 3
<211> LENGTH: 483
<212> TYPE: PRT
<213> ORGANISM: Artificial Sequence
<220> FEATURE:
<223> OTHER INFORMATION: framework of FW1.4
<220> FEATURE:
<221> NAME/KEY: MISC_FEATURE
<222> LOCATION: (24)..(73)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (277)..(326)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (341)..(390)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (423)..(472)
<223> OTHER INFORMATION: Xaa can be any naturally occurring amino acid.
      at least three and up to 50 amino acids can be present

<400> SEQUENCE: 3

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60
```

```
Xaa Xaa Xaa Xaa Xaa Xaa Xaa Xaa Xaa Trp Tyr Gln Gln Lys Pro Gly
 65                  70                  75                  80

Lys Ala Pro Lys Leu Leu Ile Tyr Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Gly Val Pro Ser Arg Phe
            130                 135             140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Phe Gly Gln Gly
            210                 215                 220

Thr Lys Leu Thr Val Leu Gly Gly Gly Gly Ser Gly Gly Gly
225                 230                 235                 240

Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Xaa Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
            325                 330                 335

Glu Trp Val Ser Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Arg Phe Thr Ile Ser Arg Asp Asn Ser Lys
385                 390                 395                 400

Asn Thr Leu Tyr Leu Gln Met Asn Ser Leu Arg Ala Glu Asp Thr Ala
            405                 410                 415

Val Tyr Tyr Cys Ala Lys Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Trp Gly Gln Gly Thr Leu Val Thr
465                 470                 475                 480
```

Val Ser Ser

<210> SEQ ID NO 4
<211> LENGTH: 232
<212> TYPE: PRT
<213> ORGANISM: Artificial Sequence
<220> FEATURE:
<223> OTHER INFORMATION: variable heavy chain framework of rFW1.4
<220> FEATURE:
<221> NAME/KEY: MISC_FEATURE
<222> LOCATION: (26)..(75)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: Xaa can be any naturally occurring amino acid.
      at least three and up to 50 amino acids can be present

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Thr Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Arg Phe Thr Ile Ser
    130                 135                 140

Arg Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 5
<211> LENGTH: 483
<212> TYPE: PRT
<213> ORGANISM: Artificial Sequence
<220> FEATURE:
<223> OTHER INFORMATION: framework of rFW1.4

-continued

```
<220> FEATURE:
<221> NAME/KEY: MISC_FEATURE
<222> LOCATION: (24)..(73)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (277)..(326)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (341)..(390)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (423)..(472)
<223> OTHER INFORMATION: Xaa can be any naturally occurring amino acid.
      at least three and up to 50 amino acids can be present

<400> SEQUENCE: 5

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly
225                 230                 235                 240

Ser Gly Gly Gly Gly Ser Gly Gly Gly Gly Ser Glu Val Gln Leu Val
```

```
                    245                 250                 255
Glu Ser Gly Gly Gly Leu Val Gln Pro Gly Gly Ser Leu Arg Leu Ser
                260                 265                 270
Cys Thr Ala Ser Xaa Xaa Xaa Xaa Xaa Xaa Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa Xaa Xaa
290                 295                 300
Xaa Xaa Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Trp Val Arg Gln Ala Pro Gly Lys Gly Leu
                325                 330                 335
Glu Trp Val Gly Xaa Xaa Xaa Xaa Xaa Xaa Xaa Xaa Xaa Xaa Xaa Xaa
            340                 345                 350
Xaa Xaa Xaa Xaa Xaa Xaa Xaa Xaa Xaa Xaa Xaa Xaa Xaa Xaa Xaa Xaa
            355                 360                 365
Xaa Xaa Xaa Xaa Xaa Xaa Xaa Xaa Xaa Xaa Xaa Xaa Xaa Xaa Xaa Xaa
            370                 375                 380
Xaa Xaa Xaa Xaa Xaa Xaa Arg Phe Thr Ile Ser Arg Asp Thr Ser Lys
385                 390                 395                 400
Asn Thr Val Tyr Leu Gln Met Asn Ser Leu Arg Ala Glu Asp Thr Ala
                405                 410                 415
Val Tyr Tyr Cys Ala Arg Xaa Xaa Xaa Xaa Xaa Xaa Xaa Xaa Xaa Xaa
            420                 425                 430
Xaa Xaa Xaa Xaa Xaa Xaa Xaa Xaa Xaa Xaa Xaa Xaa Xaa Xaa Xaa Xaa
            435                 440                 445
Xaa Xaa Xaa Xaa Xaa Xaa Xaa Xaa Xaa Xaa Xaa Xaa Xaa Xaa Xaa Xaa
450                 455                 460
Xaa Xaa Xaa Xaa Xaa Xaa Xaa Trp Gly Gln Gly Thr Leu Val Thr
465                 470                 475                 480
Val Ser Ser

<210> SEQ ID NO 6
<211> LENGTH: 232
<212> TYPE: PRT
<213> ORGANISM: Artificial Sequence
<220> FEATURE:
<223> OTHER INFORMATION: variable heavy chain framework of rFW1.4(V2)
<220> FEATURE:
<221> NAME/KEY: MISC_FEATURE
<222> LOCATION: (26)..(75)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (90)..(139)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (172)..(221)
<223> OTHER INFORMATION: Xaa can be any naturally occurring amino acid.
      at least three and up to 50 amino acids can be present

<400> SEQUENCE: 6

Glu Val Gln Leu Val Glu Ser Gly Gly Gly Leu Val Gln Pro Gly Gly
1               5                   10                  15
Ser Leu Arg Leu Ser Cys Thr Val Ser Xaa Xaa Xaa Xaa Xaa Xaa Xaa
                20                  25                  30
Xaa Xaa Xaa Xaa Xaa Xaa Xaa Xaa Xaa Xaa Xaa Xaa Xaa Xaa
            35                  40                  45
```

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Trp Val Arg Gln Ala
 65                  70                  75                  80

Pro Gly Lys Gly Leu Glu Trp Val Gly Xaa Xaa Xaa Xaa Xaa Xaa
                     85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Arg Phe Thr Ile Ser
    130                 135                 140

Lys Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 7
<211> LENGTH: 483
<212> TYPE: PRT
<213> ORGANISM: Artificial Sequence
<220> FEATURE:
<223> OTHER INFORMATION: framework of rFW1.4(V2)
<220> FEATURE:
<221> NAME/KEY: MISC_FEATURE
<222> LOCATION: (24)..(73)
<223> OTHER INFORMATION: Xaa can be any naturally occurring amino acid.
    at least three and up to 50 amino acids can be present
<220> FEATURE:
<221> NAME/KEY: MISC_FEATURE
<222> LOCATION: (89)..(138)
<223> OTHER INFORMATION: Xaa can be any naturally occurring amino acid.
    at least three and up to 50 amino acids can be present
<220> FEATURE:
<221> NAME/KEY: MISC_FEATURE
<222> LOCATION: (171)..(220)
<223> OTHER INFORMATION: Xaa can be any naturally occurring amino acid.
    at least three and up to 50 amino acids can be present
<220> FEATURE:
<221> NAME/KEY: MISC_FEATURE
<222> LOCATION: (277)..(326)
<223> OTHER INFORMATION: Xaa can be any naturally occurring amino acid.
    at least three and up to 50 amino acids can be present
<220> FEATURE:
<221> NAME/KEY: MISC_FEATURE
<222> LOCATION: (341)..(390)
<223> OTHER INFORMATION: Xaa can be any naturally occurring amino acid.
    at least three and up to 50 amino acids can be present
<220> FEATURE:
<221> NAME/KEY: MISC_FEATURE
<222> LOCATION: (423)..(472)
<223> OTHER INFORMATION: Xaa can be any naturally occurring amino acid.
    at least three and up to 50 amino acids can be present

<400> SEQUENCE: 7

Glu Ile Val Met Thr Gln Ser Pro Ser Thr Leu Ser Ala Ser Val Gly
 1               5                  10                  15

Asp Arg Val Ile Ile Thr Cys Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
            130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
            210                 215                 220

Thr Lys Leu Thr Val Leu Gly Gly Gly Gly Ser Gly Gly Gly Gly
225                 230                 235                 240

Ser Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Thr Val Ser Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Arg Phe Thr Ile Ser Lys Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa
                420                 425                 430

```
Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 8
<211> LENGTH: 20
<212> TYPE: PRT
<213> ORGANISM: Artificial Sequence
<220> FEATURE:
<223> OTHER INFORMATION: linker

<400> SEQUENCE: 8

Gly Gly Gly Gly Ser Gly Gly Gly Gly Ser Gly Gly Gly Gly Ser Gly
1               5                   10                  15

Gly Gly Gly Ser
            20

<210> SEQ ID NO 9
<211> LENGTH: 231
<212> TYPE: PRT
<213> ORGANISM: Artificial Sequence
<220> FEATURE:
<223> OTHER INFORMATION: substituted variable light chain framework of
      FW1.4
<220> FEATURE:
<221> NAME/KEY: MISC_FEATURE
<222> LOCATION: (24)..(73)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (89)..(138)
<223> OTHER INFORMATION: Xaa can be any naturally occurring amino acid.
      at least three and up to 50 amino acids can be present
<220> FEATURE:
<221> NAME/KEY: MISC_FEATURE
<222> LOCATION: (171)..(220)
<223> OTHER INFORMATION: Xaa can be any naturally occurring amino acid.
      at least three and up to 50 amino acids can be present

<400> SEQUENCE: 9

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
        130                 135                 140
```

```
Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 10
<211> LENGTH: 122
<212> TYPE: PRT
<213> ORGANISM: Artificial Sequence
<220> FEATURE:
<223> OTHER INFORMATION: VH 43_FW1.4_mod

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Gly Val Ile Ser Ser Gly Ala Thr Tyr Tyr Ala Ser Trp Ala Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
        115                 120

<210> SEQ ID NO 11
<211> LENGTH: 111
<212> TYPE: PRT
<213> ORGANISM: Artificial Sequence
<220> FEATURE:
<223> OTHER INFORMATION: VL 43_FW1.4_mod

<400> SEQUENCE: 11

Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Phe Pro Ser Arg Phe Ser Gly
    50                  55                  60

Ser Gly Ser Gly Ala Glu Phe Thr Leu Thr Ile Ser Gly Leu Glu Pro
65                  70                  75                  80

Ala Asp Phe Ala Thr Tyr Tyr Cys Gln Gln Gly Trp Ser Asp Ser Tyr
```

```
                    85                  90                  95

Val Asp Asn Leu Phe Gly Gln Gly Thr Lys Leu Thr Val Leu Gly
            100                 105                 110

<210> SEQ ID NO 12
<211> LENGTH: 119
<212> TYPE: PRT
<213> ORGANISM: Artificial Sequence
<220> FEATURE:
<223> OTHER INFORMATION: VH 511_FW1.4_mod

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Asn Thr Tyr
            20                  25                  30

Tyr Met Asn Trp Val Arg Gln Ala Pro Gly Lys Gly Leu Glu Trp Val
        35                  40                  45

Gly Ile Ile Ala Pro Asp Thr Thr Tyr Tyr Ala Ser Trp Ala Lys
    50                  55                  60

Ser Arg Ser Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ser Gly Asp Thr Thr Ala Trp Gly Ala Asp Ile Trp Gly Gln Gly
            100                 105                 110

Thr Leu Val Thr Val Ser Ser
        115

<210> SEQ ID NO 13
<211> LENGTH: 112
<212> TYPE: PRT
<213> ORGANISM: Artificial Sequence
<220> FEATURE:
<223> OTHER INFORMATION: VL 511_FW1.4_mod

<400> SEQUENCE: 13

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ala Asn Tyr Ala Tyr Ser Ala
                85                  90                  95

Gly Tyr Gly Ala Ala Phe Gly Gln Gly Thr Lys Leu Thr Val Leu Gly
            100                 105                 110

<210> SEQ ID NO 14
<211> LENGTH: 120
<212> TYPE: PRT
<213> ORGANISM: Artificial Sequence
<220> FEATURE:
<223> OTHER INFORMATION: VH 578_FW1.4_mod

<400> SEQUENCE: 14
```

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
                100                 105                 110

Gly Thr Leu Val Thr Val Ser Ser
            115                 120

<210> SEQ ID NO 15
<211> LENGTH: 111
<212> TYPE: PRT
<213> ORGANISM: Artificial Sequence
<220> FEATURE:
<223> OTHER INFORMATION: VL 578_FW1.4_mod

<400> SEQUENCE: 15

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
                100                 105                 110

<210> SEQ ID NO 16
<211> LENGTH: 119
<212> TYPE: PRT
<213> ORGANISM: Artificial Sequence
<220> FEATURE:
<223> OTHER INFORMATION: VH 534_FW1.4_mod

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Tyr Tyr
            20                  25                  30

Tyr Met Ser Trp Val Arg Gln Ala Pro Gly Lys Gly Leu Glu Trp Val
        35                  40                  45

Gly Ile Ile Gly Pro Gly Asp Tyr Thr Asp Tyr Ala Ser Trp Ala Lys
    50                  55                  60

Gly Arg Phe Thr Ile Ser Lys Asp Thr Ser Lys Asn Thr Val Tyr Leu

```
                65                  70                  75                  80
Gln Met Asn Ser Leu Arg Ala Glu Asp Thr Ala Val Tyr Tyr Cys Ala
                    85                  90                  95

Arg Gly Asp Asp Asn Ser Gly Trp Gly Glu Asp Ile Trp Gly Gln Gly
                100                 105                 110

Thr Leu Val Thr Val Ser Ser
        115

<210> SEQ ID NO 17
<211> LENGTH: 110
<212> TYPE: PRT
<213> ORGANISM: Artificial Sequence
<220> FEATURE:
<223> OTHER INFORMATION: VL 534_FW1.4_mod

<400> SEQUENCE: 17

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Trp Leu
            20                  25                  30

Ser Trp Tyr Gln Gln Lys Pro Gly Lys Ala Pro Lys Leu Leu Ile Tyr
        35                  40                  45

Lys Glu Ser Thr Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Asn Asn Tyr Asp Ser Gly Asn Asn
                85                  90                  95

Gly Phe Pro Phe Gly Gln Gly Thr Lys Leu Thr Val Leu Gly
                100                 105                 110

<210> SEQ ID NO 18
<211> LENGTH: 119
<212> TYPE: PRT
<213> ORGANISM: Artificial Sequence
<220> FEATURE:
<223> OTHER INFORMATION: VH 509_FW1.4_mod

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Tyr Met Cys Trp Val Arg Gln Ala Pro Gly Lys Gly Leu Glu Trp Val
        35                  40                  45

Gly Cys Leu Asp Tyr Val Gly Asp Thr Asp Tyr Ala Ser Trp Ala Lys
    50                  55                  60

Gly Arg Phe Thr Ile Ser Lys Asp Ala Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Asp Asp Ser Arg Gly Trp Gly Leu Asn Ile Trp Gly Gln Gly
                100                 105                 110

Thr Leu Val Thr Val Ser Ser
        115

<210> SEQ ID NO 19
<211> LENGTH: 111
```

```
<212> TYPE: PRT
<213> ORGANISM: Artificial Sequence
<220> FEATURE:
<223> OTHER INFORMATION: VL 509_FW1.4_mod

<400> SEQUENCE: 19

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Asn Ile Arg Ile Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Asn Ala His Tyr Ser Thr
                85                  90                  95

Asn Gly Gly Thr Phe Gly Gln Gly Thr Lys Leu Thr Val Leu Gly
            100                 105                 110

<210> SEQ ID NO 20
<211> LENGTH: 120
<212> TYPE: PRT
<213> ORGANISM: Artificial Sequence
<220> FEATURE:
<223> OTHER INFORMATION: VH 578rFW1.4

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30

Tyr Tyr Met Thr Trp Val Arg Gln Ala Pro Gly Lys Gly Leu Glu Trp
        35                  40                  45

Val Gly Phe Ile Asp Pro Asp Asp Pro Tyr Tyr Ala Thr Trp Ala
50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Gly Asp His Asn Ser Gly Trp Gly Leu Asp Ile Trp Gly Gln
            100                 105                 110

Gly Thr Leu Val Thr Val Ser Ser
        115                 120

<210> SEQ ID NO 21
<211> LENGTH: 111
<212> TYPE: PRT
<213> ORGANISM: Artificial Sequence
<220> FEATURE:
<223> OTHER INFORMATION: VL 578rFW1.4

<400> SEQUENCE: 21

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
```

```
                    35                   40                   45
Tyr Leu Ala Ser Thr Leu Ala Ser Gly Val Pro Ser Arg Phe Ser Gly
     50                   55                   60

Ser Gly Ser Gly Ala Glu Phe Thr Leu Thr Ile Ser Ser Leu Gln Pro
65                   70                   75                   80

Asp Asp Phe Ala Thr Tyr Tyr Cys Gln Asn Val Tyr Leu Ala Ser Thr
                 85                   90                   95

Asn Gly Ala Asn Phe Gly Gln Gly Thr Lys Leu Thr Val Leu Gly
                 100                  105                  110

<210> SEQ ID NO 22
<211> LENGTH: 119
<212> TYPE: PRT
<213> ORGANISM: Artificial Sequence
<220> FEATURE:
<223> OTHER INFORMATION: VH 511rFW1.4

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Asn Thr Tyr
                20                  25                  30

Tyr Met Asn Trp Val Arg Gln Ala Pro Gly Lys Gly Leu Glu Trp Val
            35                  40                  45

Gly Ile Ile Ala Pro Asp Asp Thr Thr Tyr Tyr Ala Ser Trp Ala Lys
        50                  55                  60

Ser Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ser Gly Asp Thr Thr Ala Trp Gly Ala Asp Ile Trp Gly Gln Gly
            100                 105                 110

Thr Leu Val Thr Val Ser Ser
        115

<210> SEQ ID NO 23
<211> LENGTH: 112
<212> TYPE: PRT
<213> ORGANISM: Artificial Sequence
<220> FEATURE:
<223> OTHER INFORMATION: VL 511rFW1.4

<400> SEQUENCE: 23

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asn Ile Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Ala Asn Tyr Ala Tyr Ser Ala
                85                  90                  95

Gly Tyr Gly Ala Ala Phe Gly Gln Gly Thr Lys Leu Thr Val Leu Gly
            100                 105                 110
```

```
<210> SEQ ID NO 24
<211> LENGTH: 122
<212> TYPE: PRT
<213> ORGANISM: Artificial Sequence
<220> FEATURE:
<223> OTHER INFORMATION: VH 43rFW1.4

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Gly Val Ile Ile Ser Ser Gly Ala Thr Tyr Tyr Ala Ser Trp Ala Lys
50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
        115                 120

<210> SEQ ID NO 25
<211> LENGTH: 111
<212> TYPE: PRT
<213> ORGANISM: Artificial Sequence
<220> FEATURE:
<223> OTHER INFORMATION: VL 43rFW1.4

<400> SEQUENCE: 25

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110

<210> SEQ ID NO 26
<211> LENGTH: 5
<212> TYPE: PRT
<213> ORGANISM: Artificial Sequence
<220> FEATURE:
<223> OTHER INFORMATION: synthetic peptide

<400> SEQUENCE: 26

Gly Gly Gly Gly Ser
1               5
```

```
<210> SEQ ID NO 27
<211> LENGTH: 15
<212> TYPE: PRT
<213> ORGANISM: Artificial Sequence
<220> FEATURE:
<223> OTHER INFORMATION: synthetic peptide

<400> SEQUENCE: 27

Gly Gly Gly Gly Ser Gly Gly Gly Ser Gly Gly Gly Gly Ser
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: synthetic peptide

<400> SEQUENCE: 28

Gly Gly Gly Ser Ser Gly Gly Gly Ser Gly Gly
1               5                   10

<210> SEQ ID NO 29
<211> LENGTH: 25
<212> TYPE: PRT
<213> ORGANISM: Artificial Sequence
<220> FEATURE:
<223> OTHER INFORMATION: synthetic peptide

<400> SEQUENCE: 29

Gly Gly Gly Gly Ser Gly Gly Gly Gly Ser Gly Gly Gly Gly Ser Gly
1               5                   10                  15

Gly Gly Gly Ser Gly Gly Gly Ala Ser
            20                  25
```